United States Patent [19]

Wright et al.

[11] 4,002,742
[45] Jan. 11, 1977

[54] 1-N-ALKYL-4,6-DI-(AMINOGLYCOSYL)-1,3-DIAMINOCYCLITOS, METHODS FOR THEIR MANUFACTURE, METHODS FOR THEIR USE AS ANTIBACTERIAL AGENTS, AND COMPOSITIONS USEFUL THEREFOR

[75] Inventors: John J. Wright, Orange; Peter J. L. Daniels, Cedar Grove; Alan K. Mallams, West Orange; Tattanahalli L. Nagabhushan, East Orange, all of N.J.

[73] Assignee: Schering Corporation, Kenilworth, N.J.

[22] Filed: July 30, 1974

[21] Appl. No.: 492,998

Related U.S. Application Data

[63] Continuation-in-part of Ser. No. 452,600, March 19, 1974, abandoned.

[52] U.S. Cl. .............................. 424/180; 536/17; 536/14
[51] Int. Cl.$^2$ ........................................ A61K 31/70
[58] Field of Search ................. 260/210 AB, 210 K

[56] References Cited

UNITED STATES PATENTS

| 3,651,042 | 3/1972 | Marquez et al. | 260/210 AB |
|---|---|---|---|
| 3,832,286 | 8/1974 | Weinstein et al. | 260/210 AB |

OTHER PUBLICATIONS

Journal of Antibiotics, vol. 21, 1968, pp. 340–349.

*Primary Examiner*—Lewis Gotts
*Assistant Examiner*—Cary Owens
*Attorney, Agent, or Firm*—Mary S. King

[57] ABSTRACT

1-N-Alkyl-4,6-di-(aminoglycosyl)-1,3-diaminocyclitols, valuable as antibacterial agents, are prepared by treating an acid addition salt of a 4,6-di-(aminoglycosyl)-1,3-diamonocyclitol antibacterial agent in an inert solvent, preferably a protic solvent containing water, with one equivalent of a hydride donor reducing agent and with at least one equivalent of an aldehyde.

The 1-N-alkyl-4,6-di-(aminoglycosyl)-1,3-diaminocyclitols are also prepared by treating the corresponding 1-N-acyl-4,6-di-(aminoglycosyl)-1,3-diaminocyclitol with an amide-reducing hydride reagent in an inert organic solvent.

Other methods of preparing 1-N-alkyl-4,6-di-(aminoglycosyl)-1,3-diaminocyclitols include carrying out the foregoing processes with partially N-protected intermediates. Another useful process involves preparing a Schiff base of the 1-amino function of a partially N-protected 4,6-di-(aminoglycosyl)-1,3-diaminocyclitol followed by reduction of said Schiff base and removal of the N-protecting groups.

Pharmaceutical compositions comprising 1-N-alkyl-4,6-di-(aminoglycosyl)-1,3-diaminocyclitols are described as well as the method of using said compositions to elicit an antibacterial response in a warm blooded animal having a susceptible bacterial infection.

47 Claims, No Drawings

1-N-ALKYL-4,6-DI-(AMINOGLYCOSYL)-1,3-DIAMINOCYCLITOS, METHODS FOR THEIR MANUFACTURE, METHODS FOR THEIR USE AS ANTIBACTERIAL AGENTS, AND COMPOSITIONS USEFUL THEREFOR

CROSS-REFERENCE TO RELATED APPLICATIONS

The application is a continuation-in-part of co-pending application U.S. Ser. No. 452,600 filed Mar. 19, 1974, and now abandoned.

FIELD OF INVENTION

This invention relates to novel compositions-of-matter, to methods for their manufacture, and to methods for their use as antibacterial agents.

More specifically, this invention relates to novel 1N-alkyl-4,6-di-(aminoglycosyl)-1,3-diaminocyclitols having antibacterial activity, to methods for their manufacture, to pharmaceutical compositions comprising said 1N-alkyl-4,6-di-(aminoglycosyl)-1,3-diaminocyclitols and to methods for their use in treating bacterial infections.

In particular, this invention relates to 1-N-alkyl derivatives of 4,6-di-(aminoglycosyl)-2-deoxystreptamine antibacterial agents including the gentamicins, sisomicin, verdamicin, tobramycin, Antibiotics G-418, 66-40B, 66-40D, JI-20A, JI-20B, G-52, and to 1-N-alkyl derivatives of related 4,6-di-(aminoglycosyl)-1,3-diaminocyclitol antibacterial agents such as mutamicins 1,2,4,5, and 6. The 1-N-alkyl derivatives of this invention include 1-N-alkyl, 1-N-alkenyl, 1-N-aralkyl, 1-N-hydroxyalkyl, 1-N-aminoalkyl, 1-N-alkylaminoalkyl, 1-N-aminohydroxyalkyl, and 1-N-alkylaminohydroxyalkyl derivatives.

This invention also relates to the processes for preparing the foregoing 1-N-alkyl-4,6-di-(aminoglycosyl)-1,3-diaminocyclitols, to pharmaceutical compositions comprising said 1-N-alkyl-4,6-di-(aminoglycosyl)-1,3-diaminocyclitols, and to the method of using said pharmaceutical compositions to elicit an antibacterial response in a warm blooded animal having a susceptible bacterial infection.

PRIOR ART

Known in the art are broad spectrum antibacterial agents which may be classified chemically as 4,6-di-(aminoglycosyl)-1,3-diaminocyclitols. Valuable antibacterial agents of this group are those wherein the aminocyclitol is 2-deoxystreptamine or a derivative thereof having amino functions at positions 1 and 3. Particularly valuable antibacterials of the 4,6-di-(aminoglycosyl)-2-deoxystreptamines are those wherein the aminoglycosyl group at the 6-position is a garosaminyl radical. Within the class of 4-aminoglycosyl-6-garosaminyl-2-deoxystreptamines are antibiotics such as gentamicins B, $B_1$, $C_1$, $C_{1a}$, $C_2$, $C_{2a}$, $C_{2b}$, and $X_2$; sisomicin, verdamicin, Antibiotic G-418, Antibiotic G-52, Antibiotic JI-20A and Antibiotic JI-20B.

By our invention we have discovered methods whereby the amino group at the 1-position of the 2-deoxystreptamine or derivative thereof in a 4,6-di-(aminoglycosyl)-1,3-diaminocyclitol is selectively N-alkylated. We have discovered also that the 1-N-alkyl-4,6-di-(aminoglycosyl)-2-deoxystreptamines or derivatives thereof thereby produced are valuable broad spectrum antibacterial agents possessing improved antibacterial activities compared to the parent antibiotics. Preferred compounds of our invention include 1-N-lower alkyl-4-aminoglycosyl-6-garosaminyl-2-deoxystreptamines having up to 4 carbon atoms, particularly the 1-N-ethyl, 1-N-propyl and 1-N-(δ-aminobutyl) derivatives, which advantageously exhibit improved antibacterial activity against organisms resistant to the parent compound, particularly valuable compounds of this invention being 1-N-ethylsisomicin and 1-N-ethylverdamicin.

GENERAL DESCRIPTION OF THE INVENTION COMPOSITION-OF-MATTER ASPECT

Included among the antibacterially active compositions-of-matter of this invention are 1-N-X-4,6-di-(aminoglycosyl)-1,3-diaminocyclitols selected from the group consisting of 1-N-X-gentamicin A, 1-N-X-gentamicin B, 1-N-X-gentamicin $B_1$, 1-N-X-gentamicin $C_1$, 1-N-X-gentamicin $C_{1a}$, 1-N-X-gentamicin $C_2$, 1-N-X-gentamicin $C_{2a}$, 1-N-X-gentamicin $C_{2b}$, 1-N-X-gentamicin $X_2$, 1-N-X-sisomicin, 1-N-X-verdamicin, 1-N-X-tobramycin, 1-N-X-Antibiotic G-418, 1-N-X-Antibiotic 66-40B, 1-N-X-Antibiotic 66-40D, 1-N-X-Antibiotic JI-20A, 1-N-X-Antibiotic JI-20B, 1-N-X-Antibiotic G-52, 1-N-X-mutamicin 1, 1-N-X-mutamicin 2, 1-N-X-mutamicin 4, 1-N-X-mutamicin 5, and 1-N-X-mutamicin 6;

wherein X is an alkyl substituent selected from the group consisting of alkyl, cycloalkyl, alkenyl, aralkyl, hydroxyalkyl, aminoalkyl, alkylaminoalkyl, aminohydroxyalkyl, and alkylaminohydroxyalkyl, said alkyl substituent preferably having up to 8 carbon atoms, the carbon atom in said alkyl substituent adjacent to the aminoglycoside nitrogen atom being unsubstituted, and when said alkyl substituent is substituted by both hydroxyl and amino functions, only one of said hydroxyl and amino functions can be attached to any one carbon atom;

and the pharmaceutically acceptable acid addition salts thereof.

Included among the alkyl substituents contemplated for the moiety X in our novel compounds are straight and branched chain alkyl groups such as ethyl, n-propyl, n-butyl, β-methylpropyl, n-pentyl, β-methylbutyl, γ-methylbutyl and β,β-dimethylpropyl: n-hexyl, γ-methylpentyl, β-ethylbutyl, γ-ethylbutyl, n-heptyl, ε-methylheptyl, β-ethylpentyl, γ-ethylpentyl, δ-ethylpentyl, γ-propylbutyl, n-octyl, iso-octyl, β-ethylhexyl, δ-ethylhexyl, ε-ethylhexyl, β-propylpentyl, γ-propylpentyl; cycloalkylalkyl groups such as cyclopropylmethyl, cyclopentylmethyl, cyclohexylmethyl and cyclopentylethyl; alkenyl groups such as β-propenyl, β-methylpropenyl, β-butenyl, β-methyl-β-butenyl, β-ethyl-β-hexenyl; aralkyl groups such as benzyl, o-tolyl, m-tolyl, p-tolyl and phenylethyl; hydroxy substituted straight and branched chain alkyl groups such as ε-hydroxypentyl, β-hydroxy-γ-methylbutyl, β-hydroxy-β-methylpropyl, δ-hydroxybutyl, β-hydroxypropyl, γ-hydroxypropyl, ω-hydroxyoctyl; amino substituted straight and branched chain alkyl groups such as ε-aminopentyl, β-aminopropyl, γ-aminopropyl, δ-aminobutyl, β-amino-γ-methylbutyl and ω-aminooctyl and mono-N-alkylated derivatives thereof such as the N-methyl, N-ethyl, and N-propyl derivatives, e.g. ε-methylaminopentyl, β-methylaminopropyl, β-ethylaminopropyl, δ-methylaminobutyl, β-methylamino-γ-methylbutyl, and ω-methylaminobutyl; amino and hydroxy disubstituted straight and branched chain alkyl groups such as β-hydroxy-ε-aminopentyl, γ-hydroxy-γ-methyl-δ-aminobutyl, β-hydroxy-δ-aminobutyl, β-hydroxy-γ-aminopropyl, and β-hydroxy-β-methyl-γ-aminopropyl; and mono-N-alkylated derivatives thereof such as β-hydroxy-ε-methyl-aminopentyl, γ-hydroxy-γ-methyl-δ-methylaminobutyl, β-hydroxy-δ-methylaminobutyl, β-hydroxy-γ-ethylaminopropyl, and β-hydroxy-β-methyl-γ-methyl aminopropyl.

Of the foregoing alkyl substituents contemplated for the moiety X, preferred are lower alkyl substitutents having up to 4 carbon atoms, especially those having 2 to 4 carbon atoms, particularly valuable derivatives being 1-N-ethyl- and 1-N-propyl-4,6-di-(aminoglycosyl)1,3-diaminocyclitols.

Our compounds are preferably 1-N-X-derivatives containing the 1,3-diaminocyclitol known as 2-deoxystreptamine, said 2-deoxystreptamine being present in all the above listed compounds of our invention except the mutamicins. The 1,3-diaminocyclitol nucleus in each of the 1-N-X-mutamicins 1, 2, 4, 5, and 6 are streptamine, 2,5-dideoxystreptamine, 2-epi-streptamine, 5-amino-2,5-dideoxystreptamine, and 5-epi-2-deoxystreptamine, respectively.

Particularly useful antibacterial agents of our invention are 1-N-X-4,6-di-(aminoglycosyl)-2-deoxystreptamines wherein the aminoglycoside radical at the 6-position is garosaminyl. Typical 1-N-X-4-aminoglycosyl-6-garosaminyl-2-deoxystreptamines of this invention are 1-N-X-gentamicin B, 1-N-X-gentamicin B₁, 1-N-X-gentamicin C₁, 1-N-X-gentamicin C₁ₐ, 1-N-X-gentamicin C₂, 1-N-X-gentamicin C₂ₐ, 1-N-X-gentamicin C₂ᵦ, 1-N-X-gentamicin X₂, 1-N-X-sisomicin, 1-N-X-verdamicin, 1-N-X-Antibiotic G-418, 1N-X-Antibiotic JI-20A, 1-N-X-Antibiotic JI-20B, and 1-N-X-Antibiotic G-52 which compounds are defined by the following structural formula I, it being understood that in the structural formulae set forth in the specification and claims herein, the undersignated substituents at the bond terminals are hydrogen atoms:

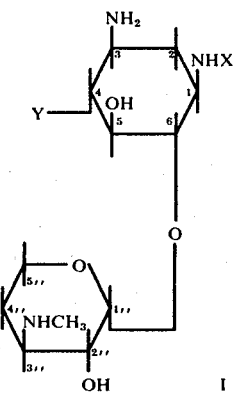

wherein X is a defined hereinabove, and wherein Y is an aminoglycosyl function selected from the group consisting of:

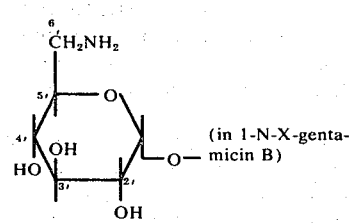
(in 1-N-X-gentamicin B)

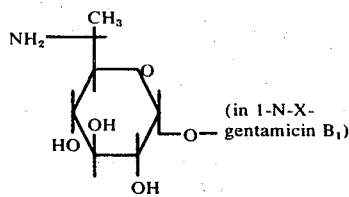
(in 1-N-X-gentamicin B₁)

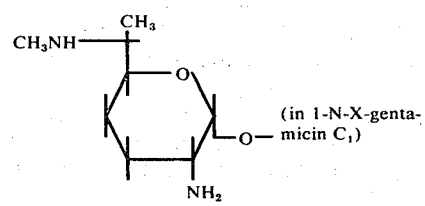
(in 1-N-X-gentamicin C₁)

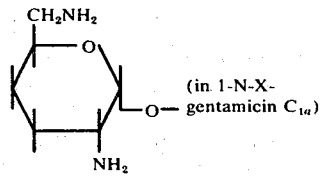
(in 1-N-X-gentamicin C₁ₐ)

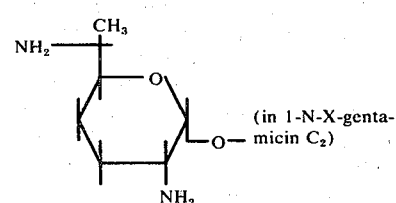
(in 1-N-X-gentamicin C₂)

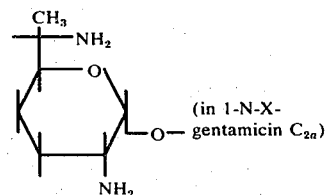
(in 1-N-X-gentamicin C₂ₐ)

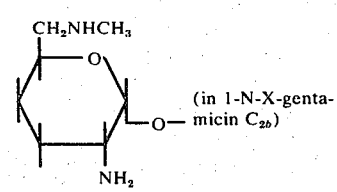
(in 1-N-X-gentamicin C₂ᵦ)

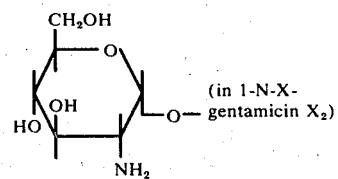
(in 1-N-X-gentamicin X₂)

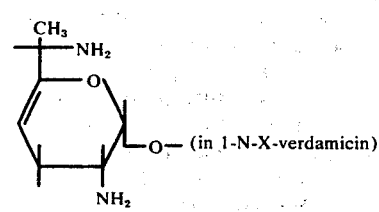 (in 1-N-X-verdamicin)

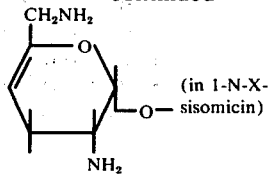 (in 1-N-X-sisomicin)

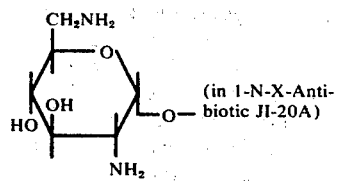 (in 1-N-X-Antibiotic JI-20A)

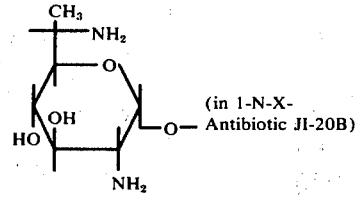 (in 1-N-X-Antibiotic JI-20B)

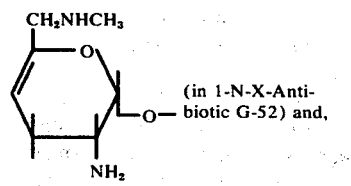 (in 1-N-X-Antibiotic G-52) and,

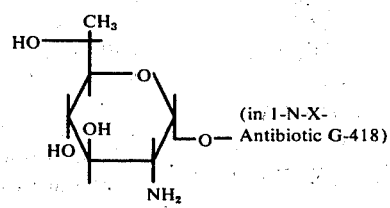 (in 1-N-X-Antibiotic G-418)

Other useful 1-N-X-4,6-di-(aminoglycosyl)-2-deoxystreptamines of this invention include 1-N-X-tobramycin of the following formula II:

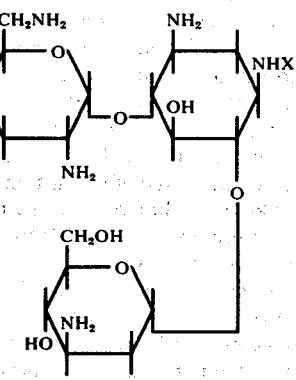

II;

1-N-X-antibiotic 66-40D of the following formula III (which are among the preferred compounds of this invention):

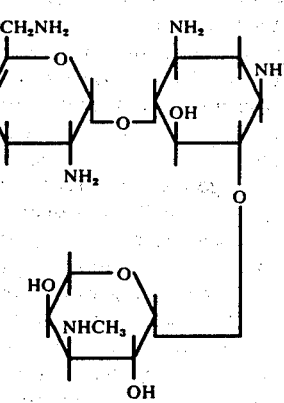

III;

and 1-N-X-gentamicin A and 1-N-X-Antibiotic 66-40B of the following formula IV:

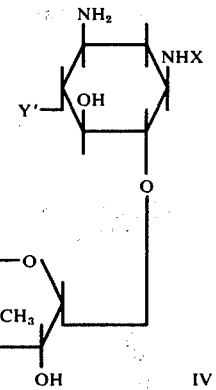

IV wherein X is as hereinabove defined and Y' is

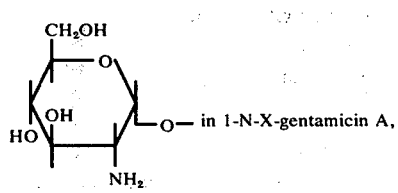 in 1-N-X-gentamicin A, and Y' is

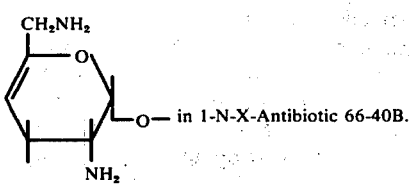 in 1-N-X-Antibiotic 66-40B.

The 1-N-X-mutamicins of this invention include 1-N-X-4-aminoglycosyl-6-garosaminyl-1,3-diaminocyclitols of the following formula V:

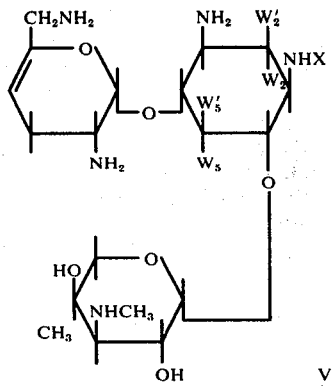

wherein X is as hereinabove defined, and in 1-N-X-mutamicin 1, $W_2'$ and $W_5$ are hydrogen and $W_2$ and $W_5'$ are hydroxy;

in 1-N-X-mutamicin 2, $W_2$, $W_2'$, $W_5$ and $W_5'$ are hydrogen;

in 1-N-X-mutamicin 4, $W_2$ and $W_5$ are hydrogen and $W_2'$ and $W_5'$ are hydroxy;

in 1-N-X-mutamicin 5, $W_2$, $W_2'$, and $W_5$ are hydrogen and $W_5'$ is amino; and 1-N-X-mutamicin 6, $W_2$, $W_2'$, and $W_5'$ are hydrogen while $W_5$ is hydroxy.

The 1-N-alkyl-4,6-di-(aminoglycosyl)-1,3-diaminocyclitols of this invention as defined by formulae I, II, III, IV and V are characterized by being white amorphous powders.

Also included within the composition-of-matter aspect of this invention are pharmaceutically acceptable acid addition salts of the 1-N-X-4,6-di-(aminoglycosyl)-1,3-diaminocyclitols such as defined by formulae I, II, III, IV and V, which salts are made according to known procedures such as by neutralizing the free base with the appropriate acid usually to about pH 5. Suitable acids for this purpose include acids such as hydrochloric, sulfuric, phosphoric, nitric, hydrobromic, acetic, propionic, maleic, ascorbic, citric, and the like. The physical embodiments of the acid addition salts of the 1-N-X-4,6-di-(aminoglycosyl)-1,3-diaminocyclitols of this invention are characterized by being white solids which are soluble in water, sparingly soluble in most polar and insoluble in most non-polar organic solvents.

The 1-N-X-4,6-di-(aminoglycosyl)-1,3-diaminocyclitols of this invention such as defined by formulae I, II, III, IV and V and their non-toxic pharmaceutically acceptable acid addition salts, in general, exhibit broad spectrum antibacterial activity and possess improved antibacterial activities compared to the parent antibiotics. This improved activity, particularly that of the 1-N-lower alkyl derivatives, is specifically manifest in the enhanced activity of the claimed compounds against organisms resistant to the parent compound. Thus, for example,, the compounds of this invention, particularly the 1-N-lower alkyl-4-aminoglycosyl-6-garosaminyl-2-deoxystreptamines, are more active against organisms which inactivate the parent antibiotics by acetylation of the 3-amino group and/or by adenylylation of the 2''-hydroxyl group. Of these, some also exhibit anti-protozoal, anti-amoebic and anthelmintic properties.

Particularly useful compounds of our invention are those wherein X is a lower alkyl having up to 8 carbon atoms, particularly those having up to 4 carbon atoms, e.g. compounds of formulae I, II, III, IV, and V wherein X is methyl, ethyl, n-propyl or n-butyl. Of these, a particularly valuable group are the 1-N-X-4-aminoglycosyl-6-garosaminyl-2-deoxystreptamines of formula I wherein X is a lower alkyl having 2 to 4 carbon atoms, particularly the 1-N-lower alkyl derivatives of gentamicin $C_1$, gentamicin $C_{1a}$, gentamicin $C_2$, gentamicin $C_{2a}$, gentamicin $C_{2b}$, sisomicin, verdamicin, and Antibiotic G-52 as well as 1-N-lower alkyl-Antibiotic 66-40D of formula III, which derivatives are broad spectrum antibacterial agents, being active against gram positive bacteria (e.g. *Staphylococcus aureus*) and gram negative bacteria (e.g. *Escherichia coli* and *Pseudomonas aeruginosa*) as determined by standard dilution tests, including bacteria resistant to the 1-N-unsubstituted precursors. Particularly useful are 1-N-ethyl-verdamicin, 1-N-(n-propyl) verdamicin, 1-N-ethyl-sisomicin, 1-N-(n-propyl) sisomicin, 1-N-(δ-aminobutyl) sisomicin and 1-N-(δ-aminobutyl) verdamicin which exhibit activity against gram negative organisms which are resistant to their 1-N-unsubstituted precursors.

GENERAL DESCRIPTION OF THE PROCESS ASPECTS OF THE INVENTION

In one process of this invention, the 1-N-X-4,6-di-(aminoglycosyl)-1,3-diaminocyclitols defined by formulae I, II, III, IV and V hereinabove, are prepared by treating an acid addition salt of the corresponding 1-N-unsubstituted-4,6-di-(aminoglycosyl)-1,3-diaminocyclitol antibacterial agent with about one molar equivalent of a hydride-donor reducing agent in an inert solvent (preferably a protic solvent in the presence of water) and in the presence of at least one molar equivalent of an aldehyde having the formula X' CHO wherein X' is a member selected from the group consisting of hydrogen and an alkyl substituent selected from the group consisting of alkyl, alkenyl, cycloalkyl, aralkyl, hydroxyalkyl, aminoalkyl, alkylaminoalkyl, aminohydroxyalkyl, and alkylaminohydroxyalkyl, said alkyl substituent having up to 7 carbon atoms, and, when said alkyl substituent is substituted by both hydroxyl and amino functions, only one of said functions can be attached to any one carbon atom.

This process, whereby the 1-amino function in an acid addition salt of a 1-N-unsubstituted-4,6-di-(aminoglycosyl)-1,3-diaminocyclitol antibacterial agent is selectively condensed with an aldehyde and concomitantly reduced in situ to form a 1-N-alkyl-4,6-di-(aminoglycosyl)-1,3-diaminocyclitol antibacterial agent, is usually carried out at room temperature in the presence of air, although it may be advantageously carried out under an inert atomsphere (e.g. argon or nitrogen). Advantageously, the reaction is completed within a short time, usually less than 30 minutes, as determined by thin layer chromatography.

Hydride-donor reducing agents useful in our process include dialkylaminoboranes (e.g. dimethylaminoborane, diethylaminoborane, and preferably morpholinoborane), teraalkylammonium cyanoborohydride (e.g. tetrabutylammonium cyanoborohydride), alkali metal borohydride (e.g. sodium borohydride) and preferably, alkali metal cyanoborohydride (e.g. lithium cyanoborohydride and sodium cyanoborohydride).

Our process is conveniently carried out at ambient temperatures in an inert solvent. By "inert solvent" is meant any organic or inorganic solvent in which the 4,6-di-(aminoglycosyl)-1,3-diaminocyclitol starting compounds and the reagents are soluble, and which will not interfere with the process under the reaction conditions thereof so there are produced a minimum of competing side reactions. Although anhydrous aprotic solvents may sometimes advantageously be employed in our process (such as tetrahydrofuran when utilizing morpholinoborane as hydride-donor reducing agent) we usually carry out our process in protic solvents, e.g. in a lower alkanol or, preferably, in water or in an aqueous lower alkanol (e.g. aqueous methanol, aqueous ethanol), although other water-miscible co-solvent systems may be employed such as aqueous dimethylformamide, aqueous hexamethylphosphoramide, aqueous tetrahydrofuran and aqueous ethylene glycol dimethyl ether.

The acid addition salts of 1-N-unsubstituted-4,6-di-(aminoglycosyl)-1,3-diaminocyclitols, requisite starting compounds of our process, may be derived from any organic acid such an acetic acid, trifluoroacetic acid, or p-toluene-sulfonic acid or from any inorganic acid such as hydrochloric acid, sulfuric acid, phosphoric acid, or nitric acid. We have found it most convenient to use the addition salts derived from sulfuric acid. In our process, optimum results are achieved when all amino groups present in the molecule are fully neutralized; however, our process may be carried out using 4,6-di-(aminoglycosyl)-1,3-diaminocyclitol acid addition salts which are not fully protonated or, alternatively, on fully protonated compounds in the presence of excess acid. In carrying out our process, we find it convenient to prepare the requisite acid addition salt starting compound in situ by adding the desired acid (e.g. sulfuric acid) to a solution or suspension of the 4,6-di-(aminoglycosyl)-1,3-diaminocyclitol (e.g. sisomicin) in a protic solvent (e.g. water) until the pH of the solution is in the range of from about 2 to about 5, preferably from about pH 2.5 to about pH 3.5. Our process proceeds best within this range, but may be carried out at pH values in the range of from about pH 1 to about pH 11.

The starting acid addition salts of this process can be derived from any 4,6-di-(aminoglycosyl)-1,3-diaminocyclitol which has a free amino group at the 1-position and which exhibits antibacterial activity against gram positive and/or gram negative organisms as determined by conventional in vitro techniques such as broth dilution tests, agar dilution tests, disc diffusion tests, and the like. A 4,6-di-(aminoglycosyl)-1,3-diaminocyclitol which inhibits bacteria at concentrations equal to or less than about 50 to about 100 mcg./ml. is considered to be an antibacterial agent.

Typical 4,6-di-(aminoglycosyl)-1,3-diaminocyclitol antibacterial precursors for the acid addition salt starting compounds of our invention include 4-aminoglycosyl-6-garosaminyl-2-deoxystreptamine antibiotics such as gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, Antibiotic G-418, Antibiotic JI-20A, Antibiotic JI-20B, and Antibiotic G-52; 4,6-di-(aminoglycosyl)-2-deoxystreptamines such as gentamicin A, tobramycin, Antibiotic 66-40B and Antibiotic 66-40D; and related 4,6-di-(aminoglycosyl)-1,3-diaminocyclitols such as mutamicin 1, mutamicin 2, mutamicin 4, mutamicin 5 and mutamicin 6. Of the foregoing, preferred starting antibiotic precursors are gentamicins B, $C_1$, $C_{1a}$, $C_2$, $C_{2a}$, $C_{2b}$, Antibiotic 66-40D, verdamicin, Antibiotic G-52, and, particularly, sisomicin, all of which lead to preferred compounds of this invention, i.e. to the corresponding 1-N-alkyl derivatives.

Most of the aforementioned 4,6-di-(aminoglycosyl)-1,3-diaminocyclitol antibiotics are known. Of the gentamicins, the starting compound referred to herein as gentamicin $X_2$ is also known in the art as gentamicin X. The starting compound referred to herein as gentamicin $C_{2a}$, isolated and characterized as set forth herein in Preparation 1, is also described and claimed in co-pending application of Peter J. L. Daniels and J. A. Marquez for *Novel Antibiotics from Micromonospora*, Ser. No. 269,914 filed July 7, 1972, now abandoned said application being of common assignee as the instant application. The starting compound referred to herein as gentamicin $C_{2b}$, isolated and characterized as set forth in Preparation 2, and having the structural formula shown herein, is named in some prior art as gentamicin $C_{2a}$.

The isolation, properties, and planar configuration of gentamicin $C_2$ is described in U.S. Pat. No. 3,651,042.

Antibiotics 66-40B and 66-40D, their preparation, isolation, properties, and planar configuration, are described in co-pending application of A. K. Mallams, R. W. Tkach, M. J. Weinstein and G. H. Wagman for *Novel Antibacterial Agents from Micromonospora Inyoensis*, U.S. Ser. No. 335,185 filed Feb. 23, 1973, now U.S. Pat. No. 3,880,828 of common assignee as the instant application. Mutamicins 1, 2, 4, 5, and 6, their preparation, isolation, properties and planar configuration, are described in co-pending application of Marvin J. Weinstein, Peter J. L. Daniels, Gerald H. Wagman, and Raymond Testa for *Mutamicins and Methods for the Preparation Thereof*, U.S. Ser. No. 443,052 filed Feb. 15, 1974, now abandoned of common assignee as the instant application.

Typical aldehydes of the formula X'CHO wherein X' is as above defined which are useful in our process include straight and branched chain alkyl aldehydes such as formaldehyde, acetaldehyde, n-propanal, n-butanal, 2-methylpropanal, n-pentanal, 2-methylbutanal, 3-methylbutanal, 2,2-dimethylpropanal, n-hexenal, 2-ethyl butanal, n-heptanal and n-octanal; cycloalkyl aldehydes such as cyclopropanecarboxaldehyde, cyclopentanecarboxaldehyde, cyclopentaneacetaldehyde, and cyclohexanecarboxaldehyde; alkenyl aldehydes such as propenal, 2-methylpropenal, 2-butenal, 2-methyl-2-butenal, 2-ethyl-2-hexenal; aralkyl aldehydes such as benzaldehyde, o, m, and p-tolualdehydes and phenylacetaldehyde; hydroxy substituted straight and branched chain alkyl aldehydes such as 5-hydroxypentanal, 2-hydroxy-3-methylbutanal, 2-hydroxy-2-methylpropanal, 4-hydroxybutanal, 2-hydroxypropanal and 8-hydroxyoctanal; amino substituted straight and branched chain alkyl aldehydes such as 5-aminopentanal, 2-aminopropanal, 3-aminopropanal, 4-aminobutanal, 2-amino-3-methylbutanal, 8-aminooctanal and mono-N-alkyl derivatives thereof; and amino and hydroxy disubstituted straight and branched chain alkyl aldehydes such as 2-hydroxy-5-aminopentanal, 3-hydroxy-3-methyl-4-aminobutanal, 2-hydroxy-4-aminobutanal, 2-hydroxy-3-aminopropanal, 2-hydroxy-2-methyl-3-aminopropanal, 2-amino-3-hydroxyoctanal, and mono-N-alkyl derivatives thereof.

In this process, if the aldehyde possesses a chiral center, one can use each enantiomer separately or together as a racemate and there will be obtained the respective diastereoisomers or a mixture thereof, respectively.

The aldehyde reagents useful in our process are either known compounds or are easily prepared from known compounds utilizing procedures well known in the art. Thus, for example, alkylaldehydes substituted by both hydroxyl and amino functions (e.g. 2-hydroxy-5-aminopentanal) may be prepared from an aminoaldehyde acetal (e.g. 4-aminobutanal diethylacetal) by protecting the amino function therein as an acetamido or phthalimido group utilizing known procedures followed by removal of the acetal function by acid hydrolysis thereby obtaining an N-protected aminoaldehyde (e.g. by converting 4-aminobutanal diethylacetal to the corresponding N-phthalimido derivative which upon acid hydrolysis yields 4-phthalimidobutanal). Treatment of the N-protected aminoaldehyde with hydrocyanic acid yields the corresponding N-protected-aminoalkyl hydroxynitrile (e.g. 2-hydroxy-5-phthalimidovaleronitrile) which upon catalytic reduction (e.g. hydrogen in the presence of palladium) or by hydride reduction (e.g. with diisobutylaluminum hydride) yields an N-protected amino-hydroxy aldehyde (e.g. 2-hydroxy-5-phthalimido-pentanal) which is an aldehyde reagent used in our process.

When carrying out our process whereby an acid addition salt of a 1-N-unsubstituted-4,6-di-(aminoglycosyl)-1,3-diaminocyclitol is treated with a hydride donor and an aldehyde, to obtain the corresponding 1-N-alkyl-4,6-di-(aminoglycosyl)-1,3-diaminocyclitol, in order to minimize competing side reactions when an aminoaldehyde is used as reagent, it is preferable to protect the amino function in the aldehyde, e.g. with an acyl blocking group such as acetamido, phthalimido, or the like, prior to carrying out our process, and thence removing the N-protecting group in the 1-N-(protected aminoalkyl)-4,6di-(aminoglycosyl)-1,3-diaminocyclitol thereby produced. It may also be advantageous to protect the hydroxyl group in hydroxyl-containing aldehydes when carrying out our process; however, it is not generally necessary.

A convenient method of carrying out our process comprises preparing a solution of a 1-N-unsubstituted-4,6-di-(aminoglycosyl)-1,3-diaminocyclitol antibacterial agent (e.g. sisomicin) in a protic solvent, (preferably water), and adjusting the pH of the solution to from about pH 2 to about pH 5 with an acid (usually dilute sulfuric acid) thereby preparing the requisite acid addition salt of the starting compound. When the pH of the solution is at about pH 5, the acid addition salt thereby produced usually contains about one equivalent of acid for each amino function in the 4,6-di-(aminoglycosyl)-1,3-diaminocyclitol (e.g. per mole of sisomicin there is present 2.5 moles of sulfuric acid). After the acid addition salt solution is prepared, there is added at least a molar equivalent, and preferably a large molar excess of the desired aldehyde (e.g. acetaldehyde) followed within a short time (usually in about 5 minutes) by the addition of about a molar equivalent (based upon the starting 4,6-di-(aminoglycosyl)-1,3-diaminocyclitol) of a hydride-donor reducing reagent, preferably an alkali metal cyanoborohydride, usually sodium cyanoborohydride. The reaction is frequently completed in less than 30 minutes as determined by thin layer chromatography and there is obtained the corresponding 1-N-alkyl-4,6-di-(aminoglycosyl)-1,3-diaminocyclitol (e.g. 1-N-ethylsisomicin) having enhanced antibacterial activity. Isolation and purification of the 1-N-alkyl derivative thereby produced is effected utilizing known techniques such as precipitation, extraction and, preferably, chromatographic techniques.

Our process thus provides a novel, convenient, onevessel process whereby an acid addition salt of an aminoglycoside is prepared in situ, and thence reacted in situ with an aldehyde (preferably in excess quantities) and with a hydride-donor-reducing agent to produce as the major product, a mono-N-alkylated derivative (e.g. 1-N-ethylsisomicin) wherein the 1-amino group attached to a secondary carbon atom is usually alkylated preferentially over other amino groups attached to primary and other secondary carbon atoms in the 4,6-di-(aminoglycosyl)-1,3-diaminocyclitol starting acid addition salt.

ANOTHER PROCESS OF THE INVENTION

The novel 1-N-alkyl-4,6-di-(aminoglycosyl)-1,3-diaminocyclitols such as defined by formulae I, II, III, IV and V are prepared by another process of this invention which comprises treating with an amide-reducing hydride reagent, in a non-reactive organic solvent, the corresponding 1-N-acyl-4,6-di-(aminoglycosyl)-1,3-diaminocyclitol, said acyl having the formula X'—CO— wherein X' is a member selected from the group consisting of hydrogen and an alkyl substituent selected from the group consisting of alkyl, cycloalkyl, alkenyl, aralkyl, hydroxyalkyl, aminoalkyl, alkylaminoalkyl, aminohydroxyalkyl, and alkylaminohydroxyalkyl, said alkyl substituent having up to 7 carbon atoms, and, when said alkyl substituent is substituted by both hydroxyl and amino functions, only one of said functions can be attached to any one carbon atom.

By non-reactive organic solvents are contemplated solvents in which The 1-N-acyl-4,6-di-(aminoglycosyl)-1,3-diaminocyclitol and the amide-reducing reagent are soluble and which will not react with the reagent so there is produced a minimum of competing side reactions. Non-reactive organic solvents which are most useful in our reduction process are ethers such as dioxane, tetrahydrofuran, DYGLYME (i.e. diethyleneglycol dimethyl ether) and the like.

Preferred amide-reducing hydride reagents are aluminum hydrides and borohydrides including lithium aluminum hydride, lithium trimethoxy-aluminum hydride, aluminum hydride, diborane, di-isoamylborane, and 9-BBN (i.e. 9-borabicyclo[3.3.1]nonane).

In general, we prefer to use diborane as the amidereducing agent except when the starting compound possesses a double bond, e.g. as in 1-N-acylsisomicin, 1-N-acylverdamicin, 1-N-acyl-Antibiotic 66-40B, 1-N-acyl-Antibiotic 66-40D, and 1-N-acyl-Antibiotic G-52, which compounds are conveniently reduced by means of lithium aluminum hydride.

The 1-N-acyl-4,6-di-(aminoglycosyl)-1,3-diaminocyclitol starting compounds are prepared according to procedures described in co-pending application Ser. No. 452,586, filed concomitantly herewith of John J. Wright for *Selective Acylation of the C-1 Amino Group of Aminoglycoside Antibiotics* and in co-pending application Ser. No. 452,571, filed concomitantly herewith of Peter J. L. Daniels for *Aminoacyl Derivatives of Aminoglycoside Antibiotics*, both of said applications being of common assignee as the instant application.

In co-pending application U.S. Ser. No. 452,586 of John J. Wright are described 1-N-acyl derivatives of 4,6-di-(aminoglycosyl)-1,3-diaminocyclitol antibiotics wherein the acyl group is unsubstituted (e.g. 1-N-acetylsisomicin and 1-N-propionylsisomicin) or substituted by a hydroxyl and/or amino function; also described are methods for their manufacture comprising reacting a partially neutralized acid addition salt of said antibiotic with an acylating agent, and isolating the 1-N-acyl derivative from the reaction mixture.

In co-pending application U.S. Ser. No. 452,571 of Peter J. L. Daniels are described 1-N-acyl-4,6-di-(aminoglycosyl)-1,3-diaminocyclitol antibacterial agents wherein said acyl function is a member selected from the group consisting of (S)-3-amino-2-hydroxypropionyl and (S)-4-amino-2-hydroxybutyryl, e.g. 1-N-( (S)-γ-amino-β-hydroxypropionyl)-sisomicin and 1-N-( (S)-δ-amino-β-hydroxybutyryl)-Antibiotic G-52, and their preparation from the corresponding 1-N-unsubstituted-4,6-di-(aminoglycosyl)-1,3-di-aminocyclitol.

In this process whereby a 1-N-acyl-4,6-di-(aminoglycosyl)-1,3-diaminocyclitol is reduced to the corresponding 1-N-alkyl derivative of the invention, if the acyl side chain of the 1-N-acylintermediate possesses a chiral center, one can use each stereoisomer separately or a mixture thereof, and there will be obtained the corresponding diastereoisomers or a mixture thereof, respectively.

OTHER PROCESSES OF THE INVENTION

Our 1-N-alkyl-4,6-di-(aminoglycosyl)-1,3-diaminocyclitols may also be prepared from the corresponding 1-N-unsubstituted-4,6-di-(aminoglycosyl)-1,3-diaminocyclitol by methods utilizing partially N-protected intermediates. Thus, for example, in the process of this invention whereby an acid addition salt of a 4,6-di-(aminoglycosyl)-1,3-diaminocyclitol is treated in an inert solvent (e.g. water) with one equivalent of a hydride-donor reducing agent, e.g. sodium cyanoborohydride, and with at least one equivalent of an aldehyde (e.g. acetaldehyde) one may utilize as starting compound a 1-N-unsubstituted-4,6-di-(aminoglycosyl)-1,3-diaminocyclitol wherein the amino function at the 6'-carbon is N-protected (e.g. the sulfuric acid addition salt of 6'N-t-butoxycarbonylsisomicin) or a 1-N-unsubstituted-4,6-di-(aminoglycosyl)-1,3-diaminocyclitol wherein the amino functions at C-2' and C-3 are N-protected (e.g. the sulfuric acid addition salt of 2',3-di-N-trifluoroacetylgentamicin $C_1$) and there will be formed the corresponding partially N-protected 1-N-alkyl derivative (e.g. 1-N-ethyl-6'-N-t-butoxycarbonylsisomicin and 1-N-ethyl-2',3-di-N-trifluoroacetylgentamicin $C_1$, respectively) which upon removal of the N-protecting groups, according to known methods, yields 1-N-alkyl compounds of this invention, e.g. 1-N-ethylsisomicin and 1-N-ethylgentamicin $C_1$, respectively.

Alternatively, our 1-N-alkyl-4,6-di-(aminoglycosyl)-1,3-diaminocyclitols are prepared by reducing a Schiff base derivative of the 1-amino function in a partially N-protected-4,6-di-(aminoglycosyl)-1,3-diaminocyclitol followed by removal of the N-protecting groups. Thus, for example, 2',3-di-N-trifluoroacetylgentamicin $C_1$ upon reaction with an aldehyde (e.g. benzaldehyde, phenylacetaldehyde or acetaldehyde) is converted to the corresponding 3'',4''-oxazolidine-1-ylidene Schiff base (e.g. 1-N-3''-N-4''-O-di-benzylidene-2',3-di-N-trifluoroacetylgentamicin $C_1$, 1-N-3''-N-4''-O-diphenethylidene-2',3-di-N-trifluoroacetylgentamicin $C_1$ and 1-N-3''-N-4''-O-diethylidene-2',3di-N-trifluroacetylgentamicin $C_1$) which, upon reduction with sodium borohydride and methanolic sodium methoxide yields the corresponding 1-N-alkyl-3'',4''-oxazolidine (e.g. 1-N-benzyl-3''-N-4''-O-benzylidenegentamicin $C_1$, 1-N-phenethyl-3''-N-4''-O-phenethylidenegentamicin $C_1$ and 1-N-ethyl-3''-N-4''-O-ethylidenegentamicin $C_1$, respectively) which upon treatment with acid yields a 1-N-alkyl compound of our invention, (e.g. 1-N-benzylgentamicin $C_1$, 1-N-phenethylgentamicin $C_1$ and 1-N-ethylgentamicin $C_1$, respectively).

In these processes, suitable as N-protecting groups are those groups known in the art to be easily removable after preparation of the 1-N-alkyl-4,6-di-(aminoglycosyl)-1,3-diaminocyclitol of our invention without affecting the 1-N-alkyl substituents therein. Exemplary of such amino protecting groups are benzyl, 4-nitrobenzyl, triphenylmethyl, 2,4-dinitrophenyl; acyl groups such as acetyl, propionyl and benzoyl; alkoxycarbonyl groups such as methoxycarbonyl, ethoxycarbonyl, 2,2,2-trichloroethoxycarbonyl, t-butoxycarbonyl and 2-iodoethoxycarbonyl; and arylalkoxycarbonyl groups such as benzyloxycarbonyl and 4-methoxybenzyloxycarbonyl groups.

Another process for the preparation of 1-N-substituted derivatives of the 4,6-di-(aminoglycosyl)-1,3-diaminocyclitols listed above wherein the substituent is straight chain alkyl having up to five carbon atoms and of the pharmaceutically acceptable acid addition salts thereof comprises reacting one of the aforementioned 4,6-di-(aminoglycosyl)-1,3-diaminocyclitols, which possesses amino-protecting groups at any position other than position 1, and wherein the 1-amino group may be activated, with an alkylating agent containing the straight chain alkyl group having up to five carbon atoms and a leaving group, removing the protecting groups and, if required, the activating group or groups present in the molecule, and isolating the derivative as such or a pharmaceutically acceptable acid addition salt.

Examples of alkylating agents advantageously used in this process are alkyl iodide, alkyl bromide, dialkyl sulfate, alkyl fluorosulphonate and alkyl p-toluenesulfonate wherein the alkyl group is the required straight chain alkyl group having up to five carbon atoms. Other alkylating agents, wherein the alkyl group preferably has one or two carbon atoms, are trialkylanilinium hydroxide, trialkyloxonium fluoroborate, trialkylsulfonium fluoroborate, or trialkylsulfoxonium fluoroborate. All of these alkylating agents contain a good leaving group, such as $Br^-$, $I^-$, $OSO_2F^-$, dialkylaniline or dialkylether.

The amino group in position 1 of the 4,6-di-(aminoglycosyl). 1,3-diaminocyclitol can be free or activated. An example of an activating group is trifluoromethylsulfonyl. These activating groups may be introduced into the molecule by reacting a 4,6-di-(aminoglycosyl)-1,3-diaminocyclitol which possesses amino-protecting groups at any position other than position 1, e.g. 3''-N-4''-O-carbonyl-2',3,6'-tri-N-t-butoxycarbonyl-sisomicin, with a compound providing the activating group, such as trifluoromethylsulfonyl chloride.

The 1-amino group can also be alkylated by way of the corresponding di-(2-cyanoethyl)-derivative which is derived by treatment with acrylonitrile of the 4,6-di-(aminoglycosyl)-1,3-di-aminocyclitol which possesses amino protecting groups at any position other than position 1. The 1-N-di-(2-cyanoethyl)-derivative thus prepared is then alkylated with one of the above listed alkylating agents followed by removal of the cyanoethyl groups.

The process of the invention is carried out under conditions similar to those employed in the well-known direct alkylation procedures of amines.

Yet other processes for the preparation of 1-N-substituted derivatives of the 4,6-di-(aminoglycosyl)-1,3-diamino-cyclitols listed above, wherein the substituent is methyl, and of the pharmaceutically acceptable acid addition salts thereof comprise reacting one of these 4,6-di-(aminoglycosyl)-1,3-di-aminocyclitols which possesses amino-protecting groups at any position other than position 1, either with formaldehyde and a cyclic imide, preferably succinimide, and treating the so-obtained compound with a hydride-donor reducing agent, preferably sodium borohydride, or with formaldehyde in the presence of formic acid, removing all protecting groups present in the molecule and isolating the derivative as such or as a pharmaceutically acceptable acid addition salt. The formation of the 1-N-methyl substituent with formaldehyde and formic acid is well known as Eschweiler-Clarke reaction.

A process for the preparation of a 1-N-substituted derivatives of the 4,6-di-(aminoglycosyl)-1,3-diaminocyclitols listed above, wherein the substituent is 2-hydroxyethyl, and of the pharmaceutically acceptable acid addition salts thereof comprises reacting one of these 4,6-di-(aminoglycosyl)-1,3-diaminocyclitols which possesses amino protecting groups at any position other than position 1, with ethylene oxide, removing all protecting groups present in the molecule and isolating the derivatives as such or as a pharmaceutically acceptable acid addition salt.

The processes described hereinabove are illustrated in detail hereinbelow in the Preparations and Examples which should not be construed as limiting the scope of our invention.

PREPARATION 1

GENTAMICIN $C_{2a}$

A. Separation of Gentamicin $C_{2a}$ from Co-produced antibiotics

Dissolved 96 gms. of gentamicin base (prepared from the sulfate salt obtained by the procedure of Example 4 of U.S. Pat. 3,091,572) in 400 ml. of the upper phase which results when methanol, chloroform and 17% ammonium hydroxide are mixed in the volume ratio of 1:2:1. Add one tenth of the solution to each of the first 10 tubes in a 500 × 80 ml. tube counter current extractor. Fill all of the tubes including the first 10 to capacity with the lower phase of the above-described solvent mixture. Set the solvent reservoir to deliver 40 ml. of upper phase to tube one (1) for each transfer. Set the apparatus for 500 transfers. When the transfers are complete, sample every eighth tube for chromatography (in duplicate) on Schleicher and Schuell paper No. 589 using the lower phase of the above-described solvent mixture. Permit the chromatograms to develop for about 16 hours then dry the papers. Plate one paper on an agar plate seeded with Staphylococcus aureus (A.T.C.C. 6538P), spray the duplicate with the conventional ninhydrin solution and heat to develop. Incubate the agar plate at 37° C overnight and combine the solution from tubes containing the material that migrates like gentamicin $C_1$ (i.e. tubes 290–360).

Replace tubes 290–360 with fresh tubes containing 40 ml. of upper phase and 40 ml. lower phase. Re-set the apparatus for an additional 2800 transfers and repeat the chromatographic procedure performed above. Combine tubes 1–16 and concentrate in vacuo to obtain 1.3 gms. of gentamicin $C_{2a}$, having the following properties:

a. a molecular weight of 463 as determined by mass spectrometry which is consistent with an empirical formula of $C_2H_{41}N_5O_7$;

b. a specific optical rotation as measured by the D line of sodium at 26° C of $+114° \pm 5°$ in water at 0.3% concentration; and c. A proton magnetic resonance (pmr) spectrum as follows: pmr(ppm) ($D_2O$); $\delta$ 0.99 (3H, d, J=6.5Hz, CH—C$\underline{H}_3$); 1.17 (3H, s, C—C$\underline{H}_3$); 2.47 (3H, s, N—C$\underline{H}_3$); 2.51 (1H, d, J=10.5Hz, H-3''); 3.75 (1H, q, J=10.5, 4Hz, H-2''); 4.00 (1H, d, J=12Hz, H-5''eq); 5.04 (1H, d, J=4Hz, H-1''); 5.13 (1H, d, J=3.5Hz, H=1').

Irradiation of the secondary methyl group at $\delta$0.99 ppm reveals H-6' as a doublet (J=6.5Hz) at $\delta$2.81 ppm.

B. Biological Activity

Gentamicin $C_{2a}$ exhibits substantially the same antibacterial spectrum in vitro as do gentamicin $C_1$, $C_{1a}$, and $C_2$. It exhibits (as the free base) about 74% of the activity of the gentamicin C complex. Thus, the antibiotic is useful for substantially the same antibacterial indications and in the same manner as disclosed in U.S. Pat. No. 3,091,572. For example, it is useful in wash solutions, for sanitary purposes, as in the washing of hands and the cleaning of equipment in contaminated rooms.

In Table 1, set forth below is shown the in vitro minimal inhibitory concentration (MIC) of gentamicin $C_{2a}$ against representative gram-positive gram-negative bacteria. The results are derived using the standard tube dilution method in Mueller-Hinton broth.

Table 1

| Organism | MIC | (mcg/ml) |
|---|---|---|
| Escherichia coli | ATCC 10536 | 0.3 |
|  | La290R55 | 17.5* |
|  | JR66 | 7.5* |
| Pseudomonas aeruginosa | 762 | 0.8 |
|  | 3223 | 0.3 |
|  | 20 | 3.0 |
|  | St 138 | > 25* |
|  | Travers | > 25* |
| Klebsiella pneumoniae | 17 | 0.8 |
|  | 3694 | 17.5* |
| Salmonella typhi. B. |  | 0.3 |
| Staphylococcus aureus | 6538P | 0.3 |
|  | Ziegler | 0.3 |
|  | 59N | 0.3 |
| Streptococcus pyogenes | C | 7.5 |
| Bacillus subtilis | 663 | 0.1 |

*Gentamicin resistant

The acute intravenous $LD_{50}$ of gentamicin $C_2a$ is 110 mg/kg when determined in male CF-1 (Carworth Farms) nice weighing 20 grams each.

PREPARATION 2

GENTAMICIN $C_{2b}$

A. Separation of Gentamicin $C_{2b}$ from Co-Produced Antibiotics

Separate the major gentamicin C components ($C_1$, $C_2$ and $C_{1a}$) as described in U.S. Pat. No. 3,651,042, Example 2, and combine those fractions containing predominantly overlaps of gentamicins $C_1$ and $C_2$ free base (500 g. of gentamicin C mixture gives 53.4 g. of overlaps). Apply 1.5 g. of this gentamicin $C_1$ and $C_2$ mixture to a column containing 50 g. of silica gel made up in a solvent system comprising chloroform: methanol: 15% ammonium hydroxide (1:2:1). Elute the column with the same solvent system and monitor the eluted fractions by thin layer chromatography on silica gel plates using the solvent system chloroform: methanol: 22% ammonium hydroxide (1:2:1) as developer. Combine those fractions containing a mixture of gentamicins $C_1$ and $C_2$ together with gentamicin $C_{2b}$ (Fractions 39–57 (410 mg.)). Rechromatograph fractions 39–57 over silica gel using a chloroform:methanol:7% ammonium hydroxide (1:2:1) solvent system and combine those fractions (98–130) containing pure gentamicin $C_{2b}$ as determined by thin layer chromatography (yield 45 mg.) having the following constants $[\alpha]_D^{26}$ +148° (c=0.3%, $H_2O$); Mass spectrum: m/e 463 (M+1)$^+$, 446, 445, 433, 350, 332, 304, 333, 305, 287, 191, 173, 163, 145, 160, 142, 118, 143; pmr(ppm) ($D_2O$): δ1.25 (3H, s, C—$CH_3$); 2.40 (3H, s, N—$CH_3$); 2.55 (3H, s, N—$CH_3$); 5.12 (1H, d, J=4Hz, H-1''); 5.22 (1H, d, J=3Hz, H-1').

Pure gentamicin $C_{2b}$ can be differentiated from gentamicin $C_1$ and $C_2$ by its mobility or thin layer chromatography using silica gel plates and a chloroform:methanol:22% ammonium hydroxide (1:2:1) solvent system as developer. The approximate Rf values in this system are as follows:

| | |
|---|---|
| gentamicin $C_1$ | 0.47 |
| gentamicin $C_2$ | 0.47 |
| gentamicin $C_{2b}$ | 0.35 |

B. Biological Activity

Gentamicin $C_{2b}$ exhibits substantially the same antibacterial spectrum in vitro as do gentamicin $C_1$, $C_{1a}$ and $C_2$. Thus, the antibiotic is useful for substantially the same antibacterial indications and in the same manner as disclosed in U.S. Pat. No. 3,091,572.

In Table 2, set forth below is shown the in vitro minimal inhibitory concentration (MIC) of gentamicin $C_{2b}$ against representative gram-positive and gram-negative bacteria. The results are derived using the standard tube dilution method in Mueller-Hinton broth.

Table 2

| Organism | | MIC (mcg/ml) |
|---|---|---|
| Escherichia coli | ATCC 10536 | 0.075 |
| | La290R55 | > 25.0* |
| | JR66 | 7.5* |
| Pseudomonas aeruginosa | 762 | 0.3 |
| | 3223 | 0.075 |
| | 20 | 0.3 |
| | St 138 | 17.5* |
| | Travers | > 25* |
| Klebsiella pneumoniae | 17 | 0.075 |
| | 3694 | 17.5* |
| Salmonella typhi. B. | | 0.3 |
| Staphylococcus aureus wood | | 0.075 |
| | Ziegler | 0.075 |
| | 59N | 0.075 |
| Streptococcus pyogenes | C | 3.0 |

Table 2-continued

| Organism | MIC (mcg/ml) |
|---|---|
| Bacillus subtilis 663 | < 0.05 |

*Gentamicin resistant.

PREPARATION 3

1-N-Acyl-4,6-Di-(Aminoglycosyl)-1,3-Diaminocyclitols

A. 1-N-Acetylsisomicin

Dissolve 1.25 g. of sisomicin sulfate in 200 ml. of methanol-water (2:3, v/v) and chill the solution. Add 1.5 ml. of acetic anhydride and after approximately 10 minutes add 0.125 ml. of triethylamine in 10 ml. of methanol over a 15 minute interval. Allow the reaction mixture to warm to room temperature over a 2 hour interval then evaporate the solvent in vacuo. Dissolve the residue in water and convert the product to the free base by passage of an aqueous solution thereof through a suitable anion exchange resin in the hydroxide ion cycle. Lyophilize the column eluate and chromatograph the residue on 50 g. of silica gel using the lower phase of 2:1:1 chloroform-methanol-7% ammonium hydroxide solvent system as eluant. Monitor the fractions via TLC and combine like fractions to obtain thereby 1-N-acetylsisomicin; M.P. 128°–130°, $[\alpha]_D^{26}$ =159° (0.3%, $H_2O$).

B. In a manner similar to that described in above Preparation 3A, other 4,6-di-(aminoglycosyl)-1,3-diaminocyclitols, e.g. verdamicin, gentamicin $C_{2a}$ and gentamicin $C_{2b}$, upon treatment with acetic anhydride and triethylamine in aqueous methanol yield the corresponding 1-N-acetyl derivatives, e.g. 1-N-acetylverdamicin, 1-N-acetylgentamicin $C_{2a}$ and 1-N-acetylgentamicin $C_{2b}$, respectively. C. In the procedure of Preparation 3a by substituting other acid anhydrides, e.g. n-octanoic acid anhydride, phenylacetic acid anhydride, propenoic acid anhydride and trans-β-phenylacrylic acid anhydride there is obtained the corresponding 1-N-acyl derivative, e.g. 1-N-(n-octanoyl)sisomicin, 1-N-phenylacetylsisomicin, 1-N-propenoylsisomicin and 1-N-(trans-β-phenylpropenoyl)sisomicin, respectively.

D. In the procedure of Preparation 3A other acid anhydrides (e.g. phenylacetic anhydride may be substituted for acetic anhydride and other 4,6-di-(aminoglycosyl)-1,3-diaminocyclitols, (e.g. verda-micin) may be substituted for sisomicin and there will be obtained the corresponding 1-N-acyl-4,6-di-(aminoglycosyl)-1,3-diaminocyclitol (e.g. 1-N-phenylacetylverdamicin).

PREPARATION 4

1-N-(Aminohydroxyacyl)-4,6-DI-(Aminoglycosyl)-1,3-Diaminocylitols

A. 1-N-(S-4-Amino-2-Hydroxybutyryl)Gentamicin $C_{1a}$
(1) 1-N-(S-4-Benzyloxycarbonylamino-2-Hydroxybutyryl) Gentamicin $C_{1a}$ Dissolve 2.8 g. (4moles) of gentamicin $C_{1a}$ sulfate in 30 ml. of water and add 15 ml. of methanol. Add 0.56 ml. (4mmoles) of triethylamine and stir for 10 minutes. Add a solution containing 4 mmoles of N-(S-4-benzyloxycarbonylamino-2-hydroxybutyryloxy) succinimide in 20 ml. of dry dimethylformamide dropwise with stirring to the antibiotic solution. Stir the mixture overnight (16hrs.) at ambient temperature. Thin layer chromatography of the reaction mixture via TLC on silica gel using the lower phase of a solvent system consisting of chloroform-methanol-ammonium hydroxide, (1:1:1), shows the presence of a plurality of minor components and one major component. Concentrate the reaction mixture to a residue in vacuo and triturate the residue with methanol to yield 3.2 g. of white solids containing all the components previously observed by chromatography.

Chromatograph 150 mg. of the product on 50 g. of silica gel using the lower phase of a solvent system consisting of chloroform-methanol-ammonium hydroxide, (2:1:1). Pool the fractions containing the major component and lyophilize to give 1-N-(S-4-benzyloxycarbonylamino-2-hydroxybutyryl)gentamicin $C_{1a}$.

(2) 1-N-(S-4-Amino-2-Hydroxybutyryl)Gentamicin $C_{1a}$

Dissolve the product of Preparation 4A(1) in a mixture consisting of 12 ml. of methanol and 3 ml. of water, add 20 mg. of 10% palladium on carbon and hydrogenate at 59 psi at room temperature. After 3 hours the reaction is essentially complete. Remove the catalyst by filtration and lyophilize the filtrate to obtain 1-N-(S-4-amino-2-hydroxybutyryl)gentamicin $C_{1a}$.

B. In the procedure of Preparation 4A the sulfate salts of other 4,6-di-(aminoglycosyl)-1,3-diaminocyclitols may be substituted for gentamicin $C_{1a}$ and other N-(S-benzyloxycarbonylaminohydroxyacyloxy)-succinimides may be substituted for N-(S-4-benzyloxycarbonylamino-2-hydroxybutyryloxy)succinimide and there will be obtained the corresponding 1-N-(aminohydroxyacyl)-4,6-di-(aminoglycosyl)-1,3-diaminocyclitol.

PREPARATION 5

Preparation of Aldehyde Intermediates

A. 2-Acetamido-3-Hydroxyoctanal

Protect the amino function in the 2-amino-3-hydroxy-octanoic acid by conversion thereof to an acetamido function, then esterify the resultant 2-acetamido-3-hydroxyoctanoic acid with methanol; reduce the resultant 2-acetamido-3-hydroxyoctanoic acid methyl ester with di-isobutylaluminum hydride according to known procedures to obtain 2-acetamido-3-hydroxyoctanal.

B. 2-Acetoxy-4-(N-Methylacetamido)Butanal

Threat the diethylacetal of 2-hydroxy-4-aminobutanal with acetic anhydride in pyridine followed by treatment of the resulting diethylacetal of 2-acetoxy-4-acetamidobutanal with sodium hydride and methyl iodide to obtain the diethylcetal of 2-acetoxy-4-(N-methylacetamido)butanal. Remove the acetal protecting group by means of acid to obtain 2-acetoxy-4-(N-methyl-acetamido)butanal.

C. 2-Acetamidoacetaldehyde

Threat 2-aminoacetaldehyde diethylacetal with acetic anhydride in pyridine, then threat the resulting 2-acetamidoacetaldehyde diethylacetal with sulfuric acid to obtain 2-acetamidoace-taldehyde.

In similar manner, treat 3-aminopropanal diethylacetal with acetic anhydride in pyridine, then threat resulting 3-acetamidopropanal diethylacetal with acid to obtain 3-acetamido-propanal.

PREPARATION 6

Selectively blocked Di-(aminoglycosyl)-1,3-diaminocyclitols

A. 2', 3,6'-Tri-N-butoxycarbonyl-3''-N-4''-O-carbonylsisomicin

1. Penta-N-carbobenzyloxysisomicin

Dissolve 25 g. of sisomicin and 13 g. of sodium carbonate in 625 ml. of distilled water. Add 100 ml. of carbobenzyloxychloride to the stirred solution at 25° C and stir the mixture for sixteen hours. Filter off the solid, wash thoroughly with water, dry in vacuo, and then wash with hexane to obtain penta-N-carbobenzyloxysisomicin (62g.) as a colorless amorphous solid. m.p. = 165°–173° C $[\alpha]_D^{26}$ + 96.2° ($CH_3OH$) IR: $\gamma$ max ($CHCL_3$) 3400, 1720, 1515, 1215, 1050, 695, $cm^-$ NMR: $\delta$ ($CDCl_3$) 1.03 (3H, broad singlet, 4''—C—$CH_3$); 3.02 (3H, broad singlet, 3''—$NCH_3$); 5.02 (10H, broad singlet, $CH_2C_6H_5$); 3.28, 3.30 ppm (25H, broad singlets, —$CH_2C_6H_5$).

2. Tetra-N-carbobenzyloxy-3''-N-4''-O-carbonylsisomicin

Dissolve 5 g. of penta-N-carbobenzyloxy-sisomicin in 50 ml. of dimethylformamide, add 250mg. of sodiumhydride to the stirred solution, and stir the reaction mixture under argon at room temperature for 2 hours. Filter and add glacial acetic acid (2 ml.) to the filtrate which is then concentrated in vacuo. Extract the residue with chloroform (200 ml., previously passed through basic alumina), wash the extract with water and dry over sodiumsulfate. The solution is evaporated to give tetra-N-carbobenzyloxy-3''-N-4''-O-carbonyl-sisomicin as an amorphous powder (3.5. g.) m.p. = 210°–213° C $[\alpha]_D^{26}$ + 68.8 (C=0.22) IR: $\nu$ max (Nujol) 3550, 1840, 1760, 1580 cm $^-$ NMR: $\delta$ ($CDCL_3$) 1.34 (3H, singlet, 4''—$CH_3$); 2.68 (3H, singlet, 3''-N-Me); 5.04 (8H, broad singlet, —$CH_2C_6H_5$).

3. 3''-N-4''-O-Carbonyl-sisomicin

To a solution of 1,3,2', 6'-tetra-N-benzyloxycarbonyl-3''-N-4''-O-carbonyl-sisomicin (10.1 g.) in tetrahydrofuran (200 ml.) add 1 litre of liquid ammonia (redistilled from sodium). To the stirred solution add 6 grams of sodium in small pieces. After stirring for 3 hours destroy the excess sodium by addition of ammonium chloride. Allow the solvents to evaporate under a stream of nitrogen. Dissolve the residue in water and pass through a medium of Amberlite IRC-50 resin ($H^+$ form) and wash the resin well with water than elute the product with 2N ammonium hydroxide solution. Evaporate the ammonia eluate in vacuo to give the title product (3''-N-4''-O-carbonyl-sisomicin). Yield ca 4 gms. IR: $\nu$ max (Nujol) 1745 $cm^{-1}$. The product may be used in subsequent steps without further purification. However a very pure sample may be obtained by chromatography of the product over silica gel using the lower phase of a chloroform:methanol:conc.ammonium hydroxide (1:1:1) solvent system as eluant.

4. 2',3,6'-Tri-N-t-butoxycarbonyl-3''-N-4''-O-carbonyl-sisomicin

Dissolve 3''-N-4''-O-carbonyl-sisomicin (1.4 g., 3 mmoles) in 10 ml. of 50% aqueous methanol containing triethylamine (3.5 mmoles). With stirring, add t-butoxycarbonyl azide (3.5 mmoles) dropwise. Stir the mixture for two days at room temperature. Add 5 ml. of Amberlite IRA-401S ($OH^-$) ion exchange resin along with 5 ml. methanol and stir for ½ hours. Remove the resin by filtration and wash with methanol. Concentrate the filtrate and chromatograph the residue on a column of silica gel (60–100 mesh, 20.0 g.) using chloroform:methanol:ammonium hydroxide (30:10:0.4) as the solvent system. Pool the homogeneous fractions containing the title material and remove the solvent by evaporation in vacuo. Dissolve the residue in methanol and precipitate with excess ether. Isolate the solid product by filtration and dry.

B. 2',3-Di-N-Trifluoroacetyl Gentamicin $C_1$ 1. 2'-N-Trifluoroacetyl Gentamicin $C_1$ Dissolve 1.7 g. of gentamicin $C_1$ in 20 ml. of methanol, cool the mixture to 4° C and add 0.46 ml. (0.563 g.) of ethyl thioltrifluoroacetate with stirring. Allow the reaction to continue for 2 hours and concentrate the solution to a residue in vacuo. Chromatograph the product on 80 g. of silica gel G using the lower phase of a mixture of chloroform:methanol:water:ammonium hydroxide in the volume ratio of 10:5:4:1 as eluant. Combine the fractions containing the major component and concentrate to obtain 1.4 g. of the title compound, m.p. 108°–111° C, $[\alpha]_D^{26} = +128°$ (c=0.3%, $H_2O$). Analysis for $C_{23}H_{42}N_5O_8F_3 \cdot H_2O$ requires C=46.69%; H=7.50%; N=11.84%; F=9.63%. Found: C=46.66%; H=7.65%; N=11.60%; F=9.24%.

2. 2',3-Di-N-Trifluoroacetyl Gentamicin $C_1$

Dissolve 0.66 g. of the product of Step 1 in 10 ml. of methanol, cool the mixture to 4° C and add 0.148 ml. (0.182 g.) of ethyl thioltrifluoroacetate dissolved in 3 ml. of methanol. Stir the reaction mixture for about 16 hours and concentrate to a residue in vacuo. Chromatograph the product on 30 g. of silica gel as described in Step 1. Monitor the column by thin layer chromatography, combine the appropriate fractions and concentrate to obtain 0.32 g. of the title compound, m.p. 121°–129° C $[\alpha]_D^{26} = 121°$ (c = 0.3%; $H_2O$). Analysis for $C_{25}H_{41}N_5O_9F_6$ requires C=44.84%; H=6.17%; N=10.46%. Found: C=44.94%; H=6.35%; N=10.17%.

C. 6'-N-Trifluoroacetyl-sisomicin

Dissolve 20 g. of sisomicin in 1.2 liters of anhydrous methanol and add dropwise a solution of 6 ml. of ethyl thioltrifluoroacetate in 60 ml. of methanol over a 3 hour period with stirring. Allow the reaction to proceed for 18 hours at room temperature and remove the solvent in vacuo to give a residue of 23.8 g. of product of approximately 95% purity having the following physicochemical properties: Mass Spectral data: m/e 543 $M^+$, other definitive peaks at m/e 413, 395, 385, 362, 223 and 126. NMR (60MHz, $D_2O$) δ 5.37 (doublet, J=2Hz, H-1'); 5.12 (doublet, J=4Hz, H-1''); 4.96 (broad singlet, H-4'); 2.57 (singlet, N—$CH_3$); 1.26 (singlet, C—$CH_3$).

D. 6'-N-t-butoxycarbonyl Gentamicin $C_{1a}$

Dissolve 2.69 g. of gentamicin $C_{1a}$ in 60 ml. of methanol: water (1:1), cool to 5° C and add 1.815 ml. of triethylamine. Add with stirring 1.91 g. of t-butoxycarbonyl azide dropwise. Stir the mixture at 5° C for 18 hours. Add 20 ml. of Amberlite IRA-401S resin ($OH^-$ form), stir for 30 minutes, filter and evaporate the filtrate to dryness in vacuo. Chromatograph the crude product over silica gel (350 g.) using the lower phase of a 2:1:1, chloroform:methanol:concentrated ammonium hydroxide solvent system as eluant. Take 3 ml. fractions and monitor their contents by TLC. Combine fractions containing the major reaction product and evaporate to obtain the title compound of this example (0.42 g., 13%), $[\alpha]_D^{26} + 137°$ ($CH_3OH$), PMR δ 1.23 (3H, s, C—$CH_3$); 1.45 (9H, s, C—$(CH_3)_3$); 2.53 (3H, s, N—$CH_3$); δ 5.08 (2H, overlapping doublets, J=3.5Hz, H-1' and H-1'') PPM. Mass spectrum m/e 550 [$(M+1)^+$] and m/e 549 ($M^+$).

E. 6'-N-t-butoxycarbonyl Gentamicin B

Dissolve 1 g. of gentamicin B in 30 ml. of 50% aqueous methanol and cool to 5° C. Add 0.297 g. of t-butoxycarbonyl azide dropwise with stirring followed by 0.186 ml. of triethylamine and stir the resulting solution for 18 hours. Evaporate the reaction mixture in vacuo to a residue and chromatograph the residue on 100 g. of silica gel using the lower phase of a 2:1:1:, chloroform-methanol-concentrated ammonium hydroxide solvent system as eluant. Collect 2 ml. fractions and monitor the column effluent by TLC. Combine fractions containing like material (fracts. 180–230) and evaporate to obtain 0.830 g. 6'-N-t-butoxycarbonyl gentamicin B having the following physical constants: PMR (60MHz,$D_2O$) δ 1.21(3H, s, C—$CH_3$); 1.42 (9H, s, C($CH_3$)$_3$); 2.53 (3H, s, N—$CH_3$); 5.2 (1H, d, J=4.5Hz, H-1''); 5.23 (1H, d, J=3.0Hz, H-1') PPM.

EXAMPLE 1

1-N-Alkylsisomicin

A. 1-N-Ethylsisomicin

To a solution of 5 gm. of sisomicin in 250 ml. of water add 1 N sulfuric acid until the pH of the solution is adjusted to about 5. To the solution of sisomicin sulfuric acid addition salt thereby formed, add 2 ml. of acetaldehyde, stir for 10 minutes, then add 0.85 gm. of sodium cyanoborohydride. Continue stirring at room temperature for 15 minutes, then concentrate solution in vacuo to a volume of about 100 ml., treat the solution with a basic ion exchange resin (e.g. Amberlite IRA 401S ($OH^-$)), then lyophilize to a residue comprising 1-N-ethylsisomicin.

Purify by chromatographing on 200 gm. of silica gel, eluting with lower phase of a chloroform-methanol-7% aqueous ammonium hydroxide (2:1:1) system. Combine the like eluates as determined by thin layer chromatography and concentrate the combined eluates of the major component in vacuo to a residue comprising 1-N-ethylsisomicin (yield 1.25 gm.). Further purify by again chromatographing on 100 gm. of silica gel eluting with a chloroform-methanol-3.5% ammonium hydroxide (1:2:1) system. Pass the combined, like eluates (as determined by thin layer chromatography) through a column of basic ion exchange resin and lyophilize the eluate to obtain 1-N-ethylsisomicin (yield 0.54 gm.); $[\alpha]_D^{26} + 164°$ (0.3%, $H_2O$); pmr (ppm) ($D_2O$): δ 1.05 (3H, t, J=7Hz, —$CH_2CH_3$); 1.19 (3H, s, —C—$CH_3$); 2.5 (3H, s, N—$CH_3$); 4.85 (1H, m, =$CH$—); 4.95 (1H, d, J=4Hz, $H_1$''); 5.33 (1H, d, J=2.5 Hz, $H_1$').

Mass Spectrum: $(M+1)^+$ m/e 476 also m/e 127, 154, 160, 173, 191, 201, 219, 256, 299, 317, 332, 345, 350, 360, 378, 390, 400.

B. In the procedure of above Example 1A instead of adding 1 N sulfuric acid to the solution of sisomicin in water until it reaches a pH of about 5, other acids may be used, such as acetic acid, trifluoroacetic acid, p-toluenesulfonic acid, hydrochloric acid, phosphoric acid, or nitric acid. The acidified aqueous solution is then treated with acetaldehyde and sodium cyanoborohydride and the resultant product is purified as described above, whereby is obtained 1-N-ethylsisomicin.

C. Alternatively, in the procedure of Example 1A replace sodium cyanoborohydride with an equivalent quantity of other hydride donor-reducing agents. For example with one of morpholinoborane, tetrabutylammonium cyanoborohydride or sodium borohydride, and there is obtained 1-N-ethylsisomicin.

D. 1-N-Methylsisomicin

To a solution of 4.64 gms. of sisomicin in 180 ml. of water add 1 N sulfuric acid until the solution is at a pH of about 5. Add 1.2 ml. of 37% aqueous formaldehyde, stir for 10 minutes then add 460 mg. of sodium cyanoborohydride. Pass the reaction solution through a column of a basic ion exchange resin (e.g. Amberlite IRA 401S (OH⁻ form)) and lyophilize. Chromatograph the resultant residue on silica gel in the lower phase of a chloroform-methanol-7% aqueous ammonium hydroxide (2:1:1) solvent mixture. Combine the like eluates containing substantially 1-N-methylsisomicin as determined by thin layer chromatograhy. Evaporate in vacuo to a residue of 1-N-methylsisomicin; $[\alpha]_D^{26}$ +153° (0.3%, H$_2$O);

Mass Spectrum: (M+1)⁺m/e 462 also m/e 127, 140, 159, 160, 177, 187, 205, 256, 285, 303, 318, 331, 336(w), 346, 376, 386.

E. 1-N-(n-propyl)sisomicin

In a manner similar to that described in Example 1A treat the sulfuric acid addition salt of sisomicin in water with propanal and sodium cyanoborohydride. Isolate and purify the resultant product in a manner similar to that described, to obtain 1-N-(n-propyl)sisomicin; $[\alpha]_D^{28}$ +140° (0.3%, H$_2$O); pmr (ppm) (D$_2$O): δ 0.83 (3H, t, J=7Hz, —CH$_2$C$\underline{H}_3$); 1.14 (3H, s, —C—C$\underline{H}_3$); 2.45 (3H, s, —N—C$\underline{H}_3$); 4.82 (1H, m, =C$\underline{H}$—); 4.90 (1H, d, J=4Hz, H$_1''$); 5.78 (1H, d, J=2Hz, H$_1'$):

Mass Spectrum: (M+1)⁺ m/e 490 also 127, 160, 168, 187, 205, 215, 233, 256, 313, 331, 346, 359, 364, 374, 404, 414.

F. 1-N-(n-butyl)sisomicin

To a solution of 3 gms. of sisomicin in 200 ml. of water add 1 N sulfuric acid until the solution is at a pH of about 3.5. Add 1.5 ml. of n-butanal, stir for 10 minutes then add 450 mg. of sodium cyanoborohydride. Continue stirring for one hour then concentrate the solution in vacuo to a volume of about 100 ml. Pass this solution through a column of a basic ion exchange resin (e.g. Amberlite IRA 401S (OH⁻) and lyophilize. Chromatograph the resultant residue on 140 gm. of silica gel in the lower phase of a chloroform-methanol-7% aqueous ammonium hydroxide (2:1:1) solvent mixture. Combine the like fractions containing 1-N-(n-butyl)sisomicin as determined by thin layer chromatography and evaporate the combined eluates in vacuo to a residue comprising 1-N-(n-butyl)sisomicin; $[\alpha]_D^{26}$ +129° (0.3%, H$_2$O), pmr(ppm) (D$_2$O) δ 0.82 (3H, t, J=7Hz, —CH$_2$C$\underline{H}_3$); 1.15 (3H, s, C—C$\underline{H}_3$); 2.46 (3H, s, —N—C$\underline{H}_3$); 4.82 (1H, m, =C$\underline{H}$—); 4.92 (1H, d, J=4Hz, H$_1''$); 5.29 (1H, d, J=2Hz, H$_1'$). Mass Spectrum: (M+1)⁺ m/e 504; also m/e 127, 160, 182, 201, 219, 229, 247, 256, 327, 345, 360, 373, 388, 418, 428.

G. Other 1-N-Alkyl, 1-N-Alkenyl and 1-N-Aralkyl Sisomicins

In the procedure of Example 1A instead of acetaldehyde substitute equivalent amounts of each of the following alkyl aldehydes:
1. 2-methylpropanal,
2. n-pentanal,
3. 3-methylbutanal,
4. 2-methylbutanal,
5. 2,2-dimethylpropanal,
6. 2-ethylbutanal,
7. n-octanal,
8. propenal,
9. 2-ethyl-2-hexenal
10. benzaldehyde, and
11. phenylacetaldehyde.
12. cyclohexanecarboxaldehyde In each case carry out the reaction in a manner similar to that described in Example 1A and isolate and purify each of the resultant products in a manner similar to that described to obtain, respectively,
1. 1-N-(=methylpropyl)sisomicin,
2. 1-N-(n-pentyl)sisomicin,
3. 1-N-(γ-methylbutyl)sisomicin,
4. 1-N-(β-methylbutyl)sisomicin,
5. 1-N-(β,β-dimethylpropyl)sisomicin,
6. 1-N-(β-ethylbutyl)sisomicin,
7. 1-N-(n-octyl)sisomicin,
8. 1-N-(β-propenyl)sisomicin,
9. 1-N-(β-ethyl-β-hexenyl)sisomicin,
10. 1-N-benzylsisomicin, and
11. 1-N-phenylethylsisomicin,
12. 1-N-cyclohexylmethylsisomicin.

H. 1-N-(Hydroxyalkyl)Sisomicins

In the procedure of Example 1A, instead of acetaldehyde, substitute equivalent amounts of each of the following aldehydes:
1. 5-hydroxypentanal,
2. 2-hydroxypropanal,
3. 2-hydroxy-3-methylbutanal,
4. 2-hydroxy-2-methylpropanal,
5. 4-hydroxybutanal,
6. 8-hydroxyoctanal, and
7. 2-hydroxy-4-pentenal.

In each case carry out the reaction in a manner similar to that described in Example 1A, and isolate and purify each of the resultant products in a manner similar to that described to obtain, respectively,
1. 1-N-(ε-hydroxypentyl)sisomicin,
2. 1-N-(β-hydroxypropyl)sisomicin,
3. 1-N-(β-hydroxy-γ-methylbutyl)sisomicin,
4. 1-N-(β-hydroxy-β-methylpropyl)sisomicin,
5. 1-N-(δ-hydroxybutyl)sisomicin,
6. 1-N-(ω-hydroxycotyl)sisomicin, and
7. 1-N-(β-hydroxy-δ-pentenyl)sisomicin.

I. 1-N-(δ-Aminobutyl)Sisomicin

Add 1 N sulfuric acid dropwise to a solution of 3 gm. of sisomicin in 120 ml. of water until the pH of the solution is adjusted to about 5. To the aqueous solution of the sulfuric acid addition salt of sisomicin thereby formed, add 60 ml. of dimethylformamide followed by a solution of 2 gm. of 4-phthalimidobutanal in 10 ml. of dimethylformamide. Continue stirring for 10 minutes then add 420 mg. of sodium cyanoborohydride. After about 20 minutes add the reaction solution to 1 liter of anhydrous methanol with stirring and collect by filtration the resultant precipitate comprising the sulfuric acid addition salt of 1-N-(δ-phthalimidobutyl)sisomicin.

Purify by dissolving the precipitate in water and passing the aqueous solution over a basic ion exchange resin. Evaporate in vacuo to a residue, chromatograph the residue over silica gel eluting with the lower phase of a chloroform-methanol-7% aqueous ammonium hydroxide (2:1:1) solvent mixture, and evaporate the combined, like eluates to a residue comprising 1-N-(δ-phthalimidobutyl)sisomicin.

To 0.5 gm. of 1-N-(δ-phthalimidobutyl)sisomicin, add 5 ml. of 5% ethanolic hydrazine hydrate and heat under reflux for 3 hours. Pour the reaction solution into a large volume of tetrahydrofuran and collect by filtration the resulting precipitate comprising 1-N-(δ-aminobutyl) sisomicin.

Alternatively, the compound of this example is prepared as follows:

(1) 4-Acetamidobutyraldehyde

Dissolve 5 gms. of 4-acetamidobutyraldehyde diethyl acetal in 75 ml. of distilled water and 5 ml. of 1 N sulfuric acid. Allow the solution to stand at room temperaure until the hydrolysis is complete as determined by thin layer chromatography. Neutralize the solution with sodium bicarbonate then saturate the solution with sodium chloride and extract with chloroform. Distill the combined chloroform extracts to a residue comprising 4-acetamidobutyraldehyde, which can be used without further purification in the following procedure.

(2) 1-N-(δ-Acetamidobutyl)sisomicin

To 3 gms. of sisomicin in 120 ml. of distilled water add 0.1 N sulfuric acid until the solution is at about pH 5. Add 6 gms. of δ-acetamidobutyraldehyde prepared as described in the proceding procedure followed, after 10 minutes, with 600 gms. of solid sodium cyanoborohydride. After 2 hours, concentrate the solution to a small volume and pour into methanol. Collect the resultant precipitate by filtration, dissolve in water and pass the aqueous solution through a column of Amberlite IRA 401-S (OH⁻) ion exchange resin. Evaporate the eluant and chromatograph the resultant residue on silica gel eluting with the lower phase of a chloroform: methanol: 7% ammonium hydroxide solvent mixture. Evaporate the eluant to a residue comprising 1-N-(δ-acetamidobutyl)sisomicin.

(3) 1-N-(δ-aminobutyl)sisomicin

Treat 1-N-(δ-acetamidobutyl)sisomicin obtained in the preceding example with 10% aqueous potassium hydroxide at 100° C for 3 hours, then neutralize with Amberlite IRC-50 ion exchange resin and elute with 2 N aqueous ammonium hydroxide. Concentrate the eluant and dissolve the resultant residue in water and lyophilize to obtain 1-N-(δ-aminobutyl)sisomicin. $[\alpha]_D^{26} + 109°$ (c=0.3%, H₂O);

Mass Spectrum: (M + 1)⁺ m/e 519 also 127, 160, 197, 216, 234, 244, 256, 262, 342, 360, 375, 388, 393, 403, 443.

J. Other 1-N-(Aminoalkyl)sisomicins and 1-N-(Hydroxyaminoalkyl)sisomicins

In a manner similar to that described in Example II, treat the sulfuric acid addition salt of sisomicin in aqueous dimethylformamide with sodium cyanoborohydride, and with each of the following amino substituted aldehydes:

1. 3-phthalimidopropanal,
2. 5-phthalimidopentanal,
3. 2-phthalimidopropanal,
4. 2-hydroxy-5-phthalimidopentanal,
5. 3-methyl-3-hydroxy-4-phthalimidobutanal,
6. 2-hydroxy-4-phthalimidobutanal,
7. 2-phthalimido-3-methylbutanal,
8. 2-hydroxy-3-phthalimidopropanal,
9. 2-hydroxy-2-methyl-3-phthalimidopropanal, and
10. 8-phthalimidooctanal.

In each case carry out the reaction in a manner similar to that described in Example 1A, and isolate and purify each of the resultant products in a manner similar to that described to obtain, respectively:

1. 1-N-(γ-phthalimidopropyl)sisomicin,
2. 1-N-(ε-phthalimidopentyl)sisomicin,
3. 1-N-(β-phthalimidopropyl)sisomicin,
4. 1-N-(β-hydroxy-ε-phthalimidopentyl)sisomicin,
5. 1-N(γ-methyl-γ-hydroxy-δ-phthalimidobutyl)sisomicin,
6. 1-N-(β-hydroxy-δ-phthalimidobutyl)sisomicin,
7. 1-N-(β-phthalimido-γ-methylbutyl)sisomicin,
8. 1-N-(β-hydroxy-γ-phthalimidopropyl)sisomicin,
9. 1-N-(β-hydroxy-β-methyl-γ-phthalimidopropyl)sisomicin,
10. 1-N-(ω-phthalimidooctyl)sisomicin.

Treat each of the foregoing N-phthalimidoalkyl sisomicin derivatives with ethanolic hydrazine hydrate as described in Example II to obtain, respectively:

1. 1-N-(γ-aminopropyl)sisomicin,
2. 1-N-(ε-aminopentyl)sisomicin,
3. 1-N-(β-aminopropyl)sisomicin,
4. 1-N-(β-hydroxy-ε-aminopentyl)sisomicin,
5. 1-N-(γ-methyl-γ-hydroxy-δ-aminobutyl)sisomicin,
6. 1-N-(β-hydroxy-δ-aminobutyl)sisomicin,
7. 1-N-(β-amino-γ-methylbutyl)sisomicin,
8. 1-N-(β-hydroxy-γ-aminopropyl)sisomicin,
9. 1-N-(β-hydroxy-β-methyl-γ-aminopropyl)sisomicin, and
10. 1-N-(ω-aminooctyl)sisomicin.

K. Alkylaminoalkylsisomicins and Other Hydroxyaminoalkylsisomicins (1) 1-N-(β-methylaminoethyl)sisomicin In a manner similar to that described in Examples 1A treat sisomicin in water with 1 N sulfuric acid and 2-(N-methylacetamido)acetaldehyde followed by sodium cyanoborohydride. Isolate the resultant product in a manner similar to that described to obtain 1-N-(β-(N-methylacetamido)ethyl)sisomicin.

Treat the foregoing N-acetylated intermediate with 10% aqueous sodium hydroxide for 3 hours at 100° C, pour the foregoing reaction solution onto Amberlite IRC 50 ion exchange resin, elute with 2 M ammonium hydroxide, concentrate the combined eluates in vacuo to a volume of about 100 ml, then lyophilize to a residue comprising 1-N-(β-methylaminoethyl)sisomicin.

(2) In the procedure described in above Example 1K(1), substitute for 2-(N-methylacetamido)acetaldehyde other aldehydes such as 2-acetamido-3-hydroxyoctanal or 2-acetamido-4-pentenal as aldehyde reagents to obtain the corresponding 1-N-(aminoalkyl)-sisomicin, e.g. 1-N-(β-amino-γ-hydroxyoctyl)sisomicin and 1-N-(β-amino-δ-pentenyl)sisomicin, respectively.

L. 1-N-(β-Aminoethyl)sisomicin and 1-N-(γ-Aminopropyl)sisomicin

In a manner similar to that described in the alternate procedure of Example 1-I, treat an aqueous solution of the sulfuric acid addition salt of sisomicin at about pH 5, with β-acetamidoacetaldehyde followed by solid sodium cyanoborohydride. Isolate and purify the resultant product in a manner similar to that described to obtain 1-N-(β-acetamidoethyl)sisomicin. Hydrolyze the 1-N- (β-acetamidoethyl)sisomicin with 10% aqueous potassium hydroxide and isolate and purify the resultant product in a manner similar to that described in Paragraph (3) of the alternate procedure of Example 1-I to obtain 1-N-(β-aminoethyl)sisomicin. Mass Spectrum: (M + 1)⁺ m/e 491, also 160, 169, 187, 206, 216, 234, 256, 283, 314, 325, 334, 347, 360, 370, 375, 405, 415.

In the above procedure, by substituting γ-acetamidopropanal for β-acetamidoacetaldehyde, there is formed 1-N-(γ -acetamidopropyl) sisomicin, which when hydrolyzed with 10% aqueous potassium hydroxide and isolated and purified in the described manner yields 1-N-($\gamma$-aminopropyl)sisomicin.

EXAMPLE 2

1-N-ALKYLGENTAMICIN $C_{1a}$

A. 1-N-Ethylgentamicin $C_{1a}$

To 5. gm. of gentamicin $C_{1a}$ in 125 ml. of water add 1 N sulfuric acid until the pH of the solution is about 5.2. Then add 2 ml. of acetaldehyde. Stir the solution for 5 minutes, then add 1 gm. of sodium cyanoborohydride. Continue stirring at room temperature for 30 minutes, concentrate the solution in vacuo to a volume of about 75 ml., pass the solution through a column of a basic ion exchange resin, (e.g. Amberlite IRA 401S (OH$^-$)), then lyophilize to a residue comprising 1-N-ethylgentamicin $C_{1a}$.

Purify by chromatographing on 200 gm. of silica gel eluting with the lower phase of a chloroform-methanol-7% aqueous ammonium hydroxide (2:1:1) system. Combine the like eluates as determined by thin layer chromatography and concentrate the combined eluates of the major component in vacuo to a residue comprising 1-N-ethylgentamicin $C_{1a}$ (yield-0.95 gm.). Further purify by again chromatographing the 1-N-ethylgentamicin $C_{1a}$ on 100 gm. of silica gel eluting with chloroform-methanol-3.5% ammonium hydroxide (1:2:1) system. Treat the combined, like eluates (as determined by thin layer chromatography) with a basic ion exchange resin and lyophilize the eluate to obtain 1-N-ethylgentamicin $C_{1a}$ (0.42 gm.), $[\alpha]_D^{26}$ + 118° (c=0.3%, H$_2$O); pmr(ppm) (D$_2$O): $\delta$1.06 (3H, t, J=7Hz, —CH$_2$CH$_3$); 1.19 (3H, s, —C—CH$_3$); 2.51 (3H, s, —N—CH$_3$); 4.97 (1H, d, J=4Hz, H$_1$''); 5.16 (1H, d, J=3.5Hz,$_1$').

Mass Spectrum (M +1)$^+$ m/e 478 also m/e 129, 154, 160, 173, 191, 201, 219, 258, 301, 317, 319, 329, 332, 347, 350, 360, 378 and 402.

B. In the procedure of Example 2A instead of using 1 N sulfuric acid to adjust the pH to about 5.2, add other acids such as acetic acid, p-tolunesulfonic acid, trifluoroacetic acid, hydrochloric acid, phosphoric acid, or nitric acid. Treat the acidified aqueous solution of gentamicin $C_{1a}$ thereby produced with acetaldehyde and sodium cyanoborohydride in a manner similar to that described in above Example 2A and isolate and purify the resultant product in a manner similar to obtain 1-N-ethylgentamicin $C_{1a}$.

C. In the procedure of Example 2A, by substituting for acetaldehyde other aldehyde reagents, e.g. formaldehyde, n-propanal, n-butanal, n-octanal, hydroxyacetaldehyde, 4-hydroxybutanal and phenylacetaldehyde there is obtained the corresponding 1-N-alkylgentamicin $C_{1a}$, e.g. 1-N-methylgentamicin $C_{1a}$, 1-N-(n-propyl)gentamicin $C_{1a}$, 1-N-(n-butyl)gentamicin $C_{1a}$, 1-N-(n-octyl)gentamicin $C_{1a}$, 1-N-($\beta$-hydroxyethyl)gentamicin $C_{1a}$, 1-N-($\delta$-hydroxybutyl)gentamicin $C_{1a}$, and 1-N-(phenylethyl)gentamicin $c_{1a}$, respectively.

EXAMPLE 3

1-N-ALKYLVERDAMICIN

A. 1-N-Ethylverdamicin

To 0.5 gm. of verdamicin in 65 ml. of water add 1 N sulfuric acid until the pH of the solution is adjusted to about pH 4.9, then add 0.2 ml. of acetaldehyde. Stir the solution for 5 minutes, add 65 g. of sodium cyanoborohydride, concentrate the solution in vacuo of about 10 ml. and pour the solution into 50 ml. of methanol with stirring. Collect by filtration the resulting precipitate comprising 1-N-ethylverdamicin. Purify by chromatographing on 100 gm. of silica gel eluting with a chloroform-methanol-3.5% ammonium hydroxide (1:2:1) system. Collect the like fractions as determined by thin layer chromatography and evaporate in vacuo the combined fractions containing the major component to a residue comprising 1-N-ethylverdamicin. Further purify by again chromatographing on 7 gm. of silica gel eluting with the lower phase of a chloroform-methanol-7% ammonium hydroxide (2:1:1) system. Combine the like eluates and evaporate in vacuo to a residue of 1-N-ethylverdamicin (yield 50 mg.);

Mass Spectrum: (M+1)$^+$ m/e 490 also m/e 141, 154, 160, 173, 191, 201, 219, 270, 313, 317(w), 331, 332, 341, 350(w), 357, 359, 360, 378, 390, 414.

B. In the procedure of above Example 3A substitute for acetaldehyde other aldehyde intermediates, e.g. formaldehyde, n-propanal, n-butanal, n-octanal, hydroxyacetaldehyde, 4-hydroxybutanal, and phenylacetaldehyde. Isolate and purify each of the resultant products in a manner similar to that to obtain, respectively, 1-N-methylverdamicin, 1-N-(n-propyl)verdamicin $[\alpha]_D^{26}$ + 122° (c=0.3%, H$_2$O); pmr (ppm) (D$_2$O):$\delta$ 0.88 (3H, t, J=7Hz, CH$_2$CH$_3$); 1.19 (3H, s, C—CH$_3$); 1.16 (3H, d, J=6Hz, CH—CH$_3$); 4.81 (1H, m,=CH—); 4.97 (1H, d, J=4.0Hz, H$_1$''); 5.30 (1H, d, J=2.0Hz, =H$_1$');

Mass Spectrum: M + 1)$^+$ m/e 528 also m/e 141, 160, 168, 187, 205, 215, 233, 270, 346, 355, 373, 504; 1-N-(n-butyl)verdamicin $[\alpha]_D^{26}$ + 121° (c=0.3%, H$_2$O); pmr (ppm) (D$_2$O): $\delta$ 0.8 (3H, t, J=6.5Hz, CH$_2$—C$_{H3}$): 2.45 (3H, s, NCH$_3$); 4.8 (1H, m, C=CH—); 4.92 (1H, d, J=4.0Hz, H$_1$''); 5.25 (1H, d, J=2.0Hz, H$_1$' );

Mass Spectrum: (M + 1)$^+$m/e 518 also m/e 141, 160, 182, 201, 219, 229, 247, 270, 341, 360, 378, 387, 388, 418, 442; 1-N-($\beta$-hydroxyethyl)verdamicin, 1-N-( $\delta$-hydroxybutyl)verdamicin, and 1-N-phenylethylverdamicin.

C. By substituting verdamicin for sisomicin in the alternate procedure of Example 1-I and in the procedures in Example 1-L, there is obtained, 1-N-($\delta$-aminobutyl)-veradamicin, 1-N-($\beta$-aminoethyl)verdamicin and 1-N-($\gamma$-aminopropyl)verdamicin, respectively.

EXAMPLE 4

1-N-ALKYLGENTAMICIN $C_1$

A. 1-N-Ethylgentamicin $C_1$

In a manner similar to that described in Example 1A treat 5 gms. of gentamicin $C_1$ in 250 ml. of water with 1 N sulfuric acid until the pH of the solution is about pH 5; then treat the acidified solution with acetaldehyde and sodium cyanoborohydride in a manner similar to that described and isolate and purify the resultant product to obtain 1-N-ethylgentamicin $C_1$, $[\alpha]_D^{26}$ +114° (c=0.3%, H$_2$O); pmr(ppm) (D$_2$O): $\delta$1.03 (3H, t, 7Hz, —CH$_2$CH$_3$); 1.03 (3H, d, J=6.5Hz —CH—CH$_3$); 1.17 (3H, s, C—CH$_3$); 2.32 (3H, s, 6' N—CH$_3$); 2.49 (3H, s, 3''—NHCH$_3$); 4.94 (1H, d, J=4Hz, H$_1$''); 5.13 (1H, d, J=3.5Hz, H$_1$' ).

Mass Spectrum: (M + 1)$^+$ m/e 506 also m/e 154, 157, 160, 173, 191, 201, 219, 286, 317, 329(w), 347, 350, 360, 375, 430.

B. In the procedure of above Example 4A in place of acetaldehyde utilize other aldehyde reagents, e.g. formaldehyde, n-propanal, n-butanal, n-octanal, hydroxyacetaldehyde, 4-hydroxybutanal and phenylacetaldehyde. Isolate and purify each of the resultant products in a manner similar to that to obtain, respectively, 1-N-methylgentamicin $C_1$, 1-N-(n-propyl)gentamicin $C_1$, 1-N-(n-butyl)-gentamicin $C_1$, 1-N-(n-octyl)gentamicin $C_1$, 1-N-($\beta$-hydroxyethyl)-gentamicin $C_1$, $[\alpha]_D^{26}$ + 98.0° (C=0.3%, $H_2O$); pmr (ppm) ($D_2O$): $\delta$ 0.99 (3h, d, J=6.5Hz, 6'—$CH_3$), 1.13 (3H, s, 4''—$CH_3$), 2.28 (3H, s, 6' — $NCH_3$), 2.45 (3H, s, 3''—$NCH_3$), 4.97 (1H, d, J=4Hz, $H_1''$) and 5.11 (1H, d, J=3.5Hz, $H_1'$);

Mass Spectrum (M + 1)$^+$ m/e 522 also m/e 446, 404, 394, 391, 376, 373, 366, 363, 348, 345, 333, 286, 235, 217, 207, 189, 160, 157; $\nu$max (KBR) 3300, 1060 cm.$^{-1}$, 1-N-($\delta$-hydroxybutyl)gentamicin $C_1$, and 1-N-(phenylethyl)-gentamicin $C_1$ $[\alpha]_D^{26}$ +99.4° (c=0.3%, $H_2O$); pmr (ppm) ($D_2O$): $\delta$ 0.99 (3H, d, J=6.5Hz, 6'—$CH_3$), 1.10 (3H, s, 4''—$CH_3$), 2.28 (3H, s, 6'—$NCH_3$), 2.43 (3H, s, 3'' —$NCH_3$), 4.88 (1H, d, J=4Hz,$H_1''$), 5.08 (1H, d, J=3.5Hz, $H_1'$) and 7.33 (5H, s, —$C_6H_5$);

Mass Spectrum (M + 1)$^+$ m/e 582 also m/e 506, 464, 454, 451, 436, 433, 426, 423, 408, 405(w), 393, 295, 286, 277, 267, 249, 160, 157; $\nu$max (KBR) 300, 1050, 1030 cm.$^{-1}$, respectively,

EXAMPLE 5

1-N-Alkyl Antibiotic G-52

A. 1-N-Ethyl Antibiotic G-52

Dissolve 875 mg. of Antibiotic G-52 in 40 ml. of distilled water and add 1 N sulfuric acid until the pH of the solution is adjusted to about 3.5. Add 0.7 ml. of acetaldehyde, stir the reaction mixture for 10 minutes then add 100 mg. of sodium cyanoborohydride. Monitor the reaction solution by thin layer chromatography, and when the starting Antibiotic G-52 appears to have completely reacted (i.e. about 10 minutes) then concentrate the solution in vacuo at about 35 to 40° C to a volume of about 10 ml. Pass the concentrated solution through a basic ion exchange resin then lyophilize to a residue comprising 1-N-ethyl Antibiotic G-52. Purify by chromatographing on a silica gel column (4' by ½" column) eluting with the lower phase of a chloroform-methanol-7% aqueous ammonium hydroxide (2:1:1) system. Combine the like eluates as determined by thin layer chromatography and concentrate the combined eluates of the major component in vacuo to a residue comprising 1-N-ethyl Antibiotic G-52 (yield 60 mg.). Further purify the overlap eluates from the foregoing chromatography by chromatographing on silica gel eluting with the lower phase of a chloroform-methanol-7% aqueous ammonium hydroxide (1:2:1) system to obtain an additional 35 mg. of residue comprising 1-N-etyl Antibiotic G-52. Pass the combined residues of 1-N-ethyl Antibiotic G-52 through a column of basic ion exchange resin (e.g. Amberlite IRA 401S) and lyophilize the eluate to obtain 1-N-ethyl Antibiotic G-52 (yield 90 mg); $[\alpha]_D^{26}$ +122.1°(c=0.3%, $H_2O$), pmr(ppm) ($D_2O$); $\delta$1.06 (3H, t, J 6.5Hz, 1N—$CH_2CH_3$); 1.21 (3H, s, 4''—C—$CH_3$); 2.30 (3H, s, 3''—N—$CH_3$); 2.50 (3H, s, 6'—N—$CH_3$); 4.94 (1H, m, $H_4'$); 4.97 (1H, d, J 4.0Hz $H_1''$); 5.34 (1H, d, J 2.5Hz, $H_1'$).

Mass Spectrum: (M+1)$^+$m/e 490 also m/e 141, 154, 160, 173, 191, 201, 219, 270, 313, 317(w), 331, 332, 341, 350, 359, 360, 378, 390, 414.

B. In the procedure of above Example 5A in place of acetaldehyde use other aldehyde reagents such as formaldehyde, n-propanol, n-butanal, n-octanal, hydroxyacetaldehyde, and phenylacetaldehyde. Isolate and purify each of the resultant products in a manner similar to that described in Example 5A to obtain, respectively, 1N-methyl-Antibiotic G-52, 1-N-(n-propyl)-Antibiotic G-52, 1-N-(n-butyl)-Antibiotic G-52, 1-N-($\beta$-hydroxyethyl)-Antibiotic G-52, 1-N-($\delta$-hydroxybutyl)-Antibiotic G-52 and 1-N-phenylethyl-Antibiotic G-52.

EXAMPLE 6

Preparation OF 1-N-ALKYL-4,6-DI-Aminoglycosyl-1,3-Di-Aminocyclitol VIA N Substituted Intermediates A. 1-N-Ethylgentamicin $C_1$ via a 2',3-di-N-substituted intermediate Dissolve 240 mg. of 2',3-di-N-trifluoroacetylgentamicin $C_1$ (prepared as described in in Preparation 6B and in cop-pending application Ser. No. 452,571 of Peter J. L. Daniels for "Aminoacyl Derivatives of Aminoglycosides" filed Mar. 19, 1974 in 10 ml. of water-methanol (2:1) and adjust the pH of the solution to about 3.5 by adding 1 N-sulfuric acid. Add 0.19 ml. of acetaldehyde, stir for 10 minutes, then add 27 mg. of sodium cyanoborohydride and stir the reaction mixture for an additional 10 minutes. Evaporate the reaction mixture in vacuo to a residue comprising 1-N-ethyl-2',3-di-N-trifluoroacetylgentamicin $C_1$. Dissolve the foregoing residue in 50 ml. of concentrated ammonium hydroxide and allow the solution to stand at room temperature for 24 hours. Evaporate the mixture in vacuo and chromatograph the resultant residue over silica gel (12 g.) eluting with the lower phase of a mixture of chloroform-methanol-10% aqueous ammonium hydroxide (2:1:1). Combine the like fractions (as determined by thin layer chromatography) and evaporate the combined eluates in vacuo to a residue comprising 1-N-ethylgentamicin $C_1$. (Yield = 80 mg.).

B. 1-N-Ethylsisomicin via a 6'-N-substituted intermediate

In a manner similar to that described in above Example 6A, treat 6'-N-t-butoxycarbonylsisomicin (prepared in a manner similar to that described in Preparation 6D in aqueous methanol with sulfuric acid, then acetaldehyde and sodium cyanoborohydride. Allow the reaction mixture to stand at room temperature for 30 minutes then evaporate in vacuo to obtain 1-N-ethyl-6'-N-t-butoxycarbonlylsisomicin. Dissolve the foregoing residue in trifluoracetic acid and allow the solution to stand for 10 minutes. Then add to an excess of anhydrous methanol, filter the resultant, precipitate of the trifluoroacetic acid salt of 1-N-ethylsisomicin and chromatograph over silica gel using the lower phase of a chloroform-methanol-ammonium hydroxide solvent system in a manner similar to that described in Example 6A to obtain 1-N-ethylsisomicin.

EXAMPLE 7

1-N-Benzylgentamicin $C_1$ Via a Tri-N-protected-1-N Schiff Base Intermediate A. Dissolve 0.3 g. of 2',3-di-N-trifluoroacetylgentamicin $C_1$ in 12 ml. of ethanol and add 0.9 ml. of benzaldehyde. Stir the reaction mixture for 3 hours then evaporate in vacuo. Dissolve the resultant residue in 0.8 ml. of chloroform and add the solution dropwise to 25 ml. of hexane-ether (3:1). Separate the resultant precipitate by filtration and dry in vacuo to obtain 1-N-3''-N-4''-O-bis-benzylidine-2',3-di-N-trifluoroacetylgentamicin $C_1$. (Yield = 0.38 g); m.p. 128°–134° C; $[\alpha]_D^{26}$ +74.6° (c=0.26%, ethanol).

B. Dissolve 1.37 g. of the product obtained in above Example 7A in 100 ml. of ethanol and add to a stirred mixture of 1.37 g. sodium methoxide and 1.94 g. of sodium borohydride in 100 ml. of ethanol. Stir for 3 hours, acidify the mixture to a pH of about 3 with hydrochloric acid then stir for an additional 16 hours. Extract the solution with ether, separate and discard the ether layer. Add ammonium hydroxide to the aqueous phase until it is basic, then evaporate in vacuo to a residue. Extract the residue with 35 ml. of hot ethanol. Combine the extracts and evaporate in vacuo. Chromatograph the resultant residue over 75 g. of silica gel eluting with the lower phase of a chloroform-methanol-ammonium hydroxide-water (2:1:0.2:0.8) solvent system. Combine like fractions as determined by thin layer chromatography and evaporate to a residue comprising 1-N-benzyl-gentamicin $C_1$, m.p. 83°–88° C, $[\alpha]_D^{26}$ +90° (c=0.3%, $H_2O$); pmr(ppm) ($D_2O$): δ1.03 (3H, d, J=7Hz, HC—$CH_3$); 1.16 (3H, s, C—$CH_3$); 2.27 (3H, s, N—$CH_3$); 2.50 (3H, s, N—$CH_3$); 4.7 ($D_2O$ + Ph$CH_2$N—); 4.92 (1H, d, J=4Hz, H-1''); 5.08 (1H, d, J=3.5Hz, H-1'); 7.43 (5H, s, aromatic H);

Mass Spectrum: $(M+1)^+$ m/e 568 also m/e 440, 437, 412, 394, 379, 281, 263, 253, 235, 160, 157.

C. In the above procedure by substituting other aldehydes, e.g. propionaldehyde or phenylacetaldehyde for benzaldehyde there is obtained the corresponding 1-N-propylgentamicin $C_1$, e.g. 1-N-phenylethylgentamicin $C_1$, respectively.

1-N-methylverdamicin via a 3''-N-4''-O-oxazolidone intermediate

1. To an aqueous solution of 1 g. of verdamicin add sodium carbonate until the pH is in the range of about 8 to 9. Add a solution of 5 g. of p-nitrophenylchlorocarbonate in 25 ml. of dimethylformamide dropwise with stirring over a period of 3 hours while maintaining the pH of the reaction mixture in the range of about 8 to 9 by adding more sodium carbonate solution. After the addition is complete, continue stirring at pH 8 to 9 for 16 hours. Evaporate the mixture in vacuo, extract the resultant residue several times with hot chloroform, combine and evaporate the extracts and chromatograph the resultant residue over 100 g. of silica gel eluting with the lower phase of a (2:1:1) chloroform-methanol-concentrated ammonium hydroxide solvent system. Combine and evaporate the like fractions as determined by thin layer chromatography to obtain 3''-N-4''-O-carbonyl-verdamicin.

2. In a manner similar to that described in Example 1D treat the foregoing oxazolidone derivative in water with sulfuric acid, formaldehyde, and sodium cyanoborohydride. Isolate and purify the resultant product in a manner similar to that described to obtain 1-N-methyl-3''-N-4''-O-carbonylverdamicin.

3. Dissolve 0.2 g. of 1-N-methyl-3''-N-4''-O-carbonyl-verdamicin in 10 ml. of 2N sodium hydroxide solution. Heat under reflux for 5 hours, neutralize the reaction solution with acetic acid and evaporate to a residue. Chromatograph the residue over 10 g. of silica gel eluting with the lower phase of a (2:1:1) mixture of chloroform-methanol-15% ammonium hydroxide. Combine and evaporate like fractions as determined by thin layer chromatography to a residue to obtain 1-N-methylverdamicin.

4. In the above procedures, by substituting sisomicin for verdamicin there is prepared 3''-N-4''-O-carbonylsisomicin which upon treatment with sulfuric acid formaldehyde, and sodium cyanoborohydride yields 1-N-methyl-3''-N-4''O-carbonylsisomicin which upon hydrolysis with sodium hydroxide in the described manner yields 1-N-methylsisomicin.

D. 1-N-ethylverdamicin via a 2',3-di-N-substituted intermediate

The requisite intermediate i.e. 2',3--di-t-butoxy-carbonylverdamicin is prepared in a manner similar to the procedure described in Preparation 6B by reacting verdamicin with 2.5 molar equivalents of t-butoxycarbonylazide and chromatographing the resulting product. In a manner similar to that described in above Example 6A treat 2',3-di-N-t-butoxy-carbonylverdamicin and aqueous methanol with sulfuric acid, acetaldehyde and sodium cyanoborohydride. Isolate the resultant product in a manner similar to that described to obtain 2',3-di-N-t-butoxycarbonyl-1-N-ethylverdamicin. Remove the t-butoxy-carbonyl groups with trifluoroacetic acid in a manner similar to that described in Example 6B and isolate and purify the resultant product to obtain 1-N-ethylverdamicin.

EXAMPLE 8

1-N-Alkyl-4,6-Diaminoglycosyl-1,3-Diaminocyclitols Prepared By Hydride Reduction of the Corresponding 1-N-Acyl Derivatives A. 1-N-(S-δ-amino-β-hydroxybutyl)gentamicin $C_1$ 1. Suspend 98 mg. of 1-N-(Sδ-amino-β-hydroxybutyryl)gentamicin $C_1$ in 8 ml. of tetrahydrofuran. Add 14 ml. of N diborane in tetrahydrofuran and heat at reflux temperature for 6 hours under an atmosphere of nitrogen. Carefully add 2 ml. of water to decompose any excess diborane and evaporate. Dissolve the resultant residue in hydrazine hydrate and heat at reflux temperature under an atmosphere of nitrogen for 16 hours. Evaporate the solution and extract the residue with hot aqueous ethanol. Evaporate the combined ethanol extracts and chromatograph the resultant residue over 10 ml. of silica gel eluting with the lower phase of a chloroform-methanol-concentrated ammonium hydroxide (2:1:1) solvent system. Combine and evaporate the like fractions as determined by thin layer chromatography to obtain 1-N-(S-δ-amino-β-hydroxybutyl)gentamicin $C_1$ (yield 14.5 mg.) M.P. 93°—98° C, $[\alpha]_D^{26}$ +72.4° (c=0.35%, $H_2O$); pmr(ppm)($D_2O$) δ1.18 (3H, d, J=7Hz, CH—$CH_3$); 1.24 (3H, s, C—$CH_3$); 2.49 (3H, s, N—$CH_3$); 2.54 (3H, s, N—$CH_3$); 5.07 (1H, d, J=3.5Hz, H-1''); 5.24 (1H, d, J=3.5Hz, H-1').

Mass Spectrum: $(M+1)^+$m/e 565 also m/e 528, 516, 490, 437, 434, 410, 397, 278, 250, 232, 160, 157.

2. In the above procedure substitute 1-N-(S-γ-amino-β-hydroxypropionyl)gentamicin $C_1$ for 1-N-(S-δ-amino-β-hydroxybutyryl)gentamicin $C_1$ to obtain 1-N-(S-γ-amino-β-hydroxypropyl)gentamicin $C_1$.

3. Treat each of the following 1-N-(S-δ-amino-β-hydroxybutyryl)-4,6-diaminoglycosyl-1,3-diaminocyclitols with diborane in tetrahydrofuran in the manner described in Example 8A(1):

1. 1-N(S-δ-amino-β-hydroxybutyryl)gentamicin A,
2. 1-N-(S-δ-amino-β-hydroxybutyryl)gentamicin B,
3. 1-N-(S-δ-amino-β-hydroxybutyryl)gentamicin $B_1$,
4. 1-N-(S-δ-amino-β-hydroxybutyryl)gentamicin $C_{1a}$,
5. 1-N-(S-δ-amino-β-hydroxybutyryl)gentamicin $C_2$,
6. 1-N-(S-δ-amino-β-hydroxybutyryl)gentamicin $C_{2a}$, 7. 1-N-(S-δ-amino-β-hydroxybutyryl)gentamicin $C_{2b}$,
8. 1-N-(S-δ-amino-β-hydroxybutyryl)gentamicin $X_2$,
9. 1-N-(S-δ-amino-β-hydroxybutyryl)tobramycin,
10. 1-N-(S-δ-amino-β-hydroxybutyryl)Antibiotic G-418,
11. 1-N-(S-δ-amino-β-hydroxybutyryl)Antibiotic JI-20A,
12. 1-N-(S-δ-amino-β-hydroxybutyryl)Antibiotic JI-20B.

Isolate and purify each of the resultant products in a manner similar to that described in Example 8A (1) to obtain, respectively,
1. 1-N-(S-δ-amino-β-hydroxybutyl)gentamicin A,
2. 1-N-(S-δ-amino-β-hydroxybutyl)gentamicin B,
3. 1-N-(S-δ-amino-β-hydroxybutyl)gentamicin $B_1$,
4. 1-N-(S-δ-amino-β-hydroxybutyl)gentamicin $C_{1a}$,
5. 1-N-(S-δ-amino-β-hydroxybutyl)gentamicin $C_2$,
6. 1-N-(S-δ-amino-β-hydroxybutyl)gentamicin $C_{2a}$,
7. 1-N-(S-δ-amino-β-hydroxybutyl)gentamicin $C_{2b}$,
8. 1-N-(S-δ-amino-β-hydroxybutyl)gentamicin $X_2$,
9. 1-N-(S-δ-amino-β-hydroxybutyltobramycin,
10. 1-N-(S-δ-amino-β-hydroxybutyl)Antibiotic G-418,
11. 1-N-(S-δ-amino-β-hydroxybutyl)Antibiotic JI-20A,
12. 1-N-(S-δ-amino-β-hydroxybutyl)Antibiotic JI-20B.

4. In the procedure of Example 8A(3) hereinabove utilize as starting compounds the corresponding 1-N-(S-γ-amino-β-hydroxypropionyl) derivatives to obtain the corresponding 1-N-(S-γ-amino-β-hydroxypropyl) derivatives, i.e.
1. 1-N-(S-γ-amino-β-hydroxypropyl)gentamicin A,
2. 1-N-(S-γ-amino-β-hydroxypropyl)gentamicin B,
3. 1-N-(S-γ-amino-β-hydroxypropyl)gentamicin $B_1$,
4. 1-N-(S-γ-amino-β-hydroxypropyl)gentamicin $C_{1a}$,
5. 1-N-(S-γ-amino-β-hydroxypropyl)gentamicin $C_2$,
6. 1-N-(S-γ-amino-β-hydroxypropyl)gentamicin $C_{2a}$,
7. 1-N-(S-γ-amino-β-hydroxypropyl)gentamicin $C_{2b}$,
8. 1-N-(S-γ-amino-β-hydroxypropyl)gentamicin $X_2$,
9. 1-N-(S-γ-amino-β-hydroxypropyl)tobramycin,
10. 1-N-(S-γ-amino-β-hydroxypropyl)Antibiotic G-418,
11. 1-N-(S-γ-amino-β-hydroxypropyl)Antibiotic JI-20A,
12. 1-N-(S-γ-amino-β-hydroxypropyl)Antibiotic JI-20B.

B. 1-N-Ethylgentamicin $C_1$

1. In a manner similar to that described in Example 8A(1) treat 1-N-acetylgentamicin $C_1$ with diborane in tetrahydrofuran. Isolate and purify the resultant products in a manner similar to that described in Example A(1) to obtain 1-N-ethylgentamicin $C_1$.

2. Treat the following 1-N-acetyl-4,6-diaminoglycosyl-1,3-diaminocyclitols in the manner of above Example 8B(1):
1. 1-N-acetylgentamicin A,
2. 1-N-acetylgentamicin B,
3. 1-N-acetylgentamicin $B_1$,
4. 1-N-acetylgentamicin $C_{1a}$,
5. 1-N-acetylgentamicin $C_2$,
6. 1-N-acetylgentamicin $C_{2a}$,
7. 1-N-acetylgentamicin $C_{2b}$,
8. 1-N-acetylgentamicin $X_2$,
9. 1-N-acetyltobramycin,
10. 1-N-acetyl Antibiotic G-418,
11. 1-N-acetyl Antibiotic JI-20A,
12. 1-N-acetyl Antibiotic JI-20B.

Isolate and purify each of the resultant products in the manner similar to that described to obtain, respectively,
1. 1-N-ethylgentamicin A,
2. 1-N-ethylgentamicin B,
3. 1-N-ethylgentamicin $B_1$,
4. 1-N-ethylgentamicin $C_{1a}$,
5. 1-N-ethylgentamicin $C_2$,
6. 1-N-ethylgentamicin $C_{2a}$,
7. 1-N-ethylgentamicin $C_{2b}$,
8. 1-N-ethylgentamicin $X_2$,
9. 1-N-ethyltobramycin,
10. 1-N-ethyl Antibiotic G-418,
11. 1-N-ethyl Antibiotic JI-20A,
12. 1-N-ethyl Antibiotic JI-20B.

C. 1-N-Ethyl sisomicin

1. Suspend 1 gm. of 1 N-acetylsisomicin in 100 ml. of tetrahydrofuran. Add 1 gm. of lithium aluminum hydride, then stir the resultant suspension at reflux temperature for 24 hours under an atmosphere of nitrogen. Cool and decompose the excess hydride by careful addition of ethyl acetate. Evaporate the reaction mixture to a small volume and dilute with water. Separate the insoluble solids by filtration and wash well with acetic acid. Evaporate the combined filtrate and washings and dissolve the resultant residue in water. Adjust the pH of the aqueous solution to about 7 by addition of ammonium hydroxide. Pass the solution through a column of IRC 50 resin in the ammonium cycle and wash the column well with water. Elute with 0.5 N ammonium hydroxide, evaporate the eluate, and chromatograph the resultant residue over 20 gm. of silica gel eluting with the lower phase of a 2:1:1 chloroform-methanol-concentrated ammonium hydroxide solvent system. Combine and evaporate the like fractions as determined by thin layer chromatography to obtain 1-N-ethylsisomicin.

2. Treat the following 4,6-diaminoglycosyl-1,3-diaminocyclitols in the manner described in the procedure of Example 7C(1):
1. 1-N-acetylverdamicin,
2. 1-N-acetyl Antibiotic 66-40B,
3. 1-N-acetyl Antibiotic 66-40D,
4. 1-N-acetyl Antibiotic G-52
5. 1-N-acetylmutamicin 1,
6. 1-N-acetylmutamicin 2,
7. 1-N-acetylmutamicin 4,
8. 1-N-acetylmutamicin 5,
9. 1-N-acetylmutamicin 6.

Isolate and purify each of the resultant products to obtain, respectively,
1. 1-N-ethylverdamicin,
2. 1-N-ethyl Antibiotic 66-40B,
3. 1-N-ethyl Antibiotic 66-40D,
4. 1-N-ethyl Antibiotic G-52,
5. 1-N-ethylmutamicin 1,
6. 1-N-ethylmutamicin 2,
7. 1-N-ethylmutamicin 4,
8. 1-N-ethylmutamicin 5,
9. 1-N-ethylmutamicin 6.

D. 1-N-Methylgentamicin $C_1$

1. Dissolve 1gm. of 2′,3-di-N-trifluoroacetylgentamicin $C_1$ in 30 ml. of 50% aqueous methanol. Cool to 5° C then add 0.25 gm. of t-butoxycarbonyl azide dropwise with stirring followed by 0.155 ml. of triethylamine. Stir the resultant solution for 18 hours, evaporate the reaction mixture in vacuo to a residue and chromatograph the residue on 100 gm. of silica gel eluting with the lower phase of 2:1:1, chloroform-methanol-concentrated ammonium hydroxide solvent system. Combine and evaporate the like fractions of the major product as determined by thin layer chromatography to obtain 1-N-t-butoxycarbonyl-2′,3-di-N-trifluoroacetygentamicin $C_1$.

2. Dissolve the product of Example 8D(1) in a mixture comprising 30 ml. of methanol and 20 ml. of concentrated ammonium hydroxide. Allow the solution to stand for 3 days at room temperature, then evaporate to a residue comprising 1-N-t-butoxycarbonylgentamicin $C_1$.

3. Dissolve 100 mg. of 1-N-t-butoxycarbonylgentamicin $C_1$ in 15 ml. of 1 M diborane in tetrahydrofuran. Reflux the resultant solution for 16 hours under an atmosphere of nitrogen. Add 2 ml. of water to decompose any excess diborane and evaporate the mixture to a residue. Dissolve the residue in 10 ml. of hydrazine hydrate and heat at reflux temperature under an atmosphere of nitrogen for 16 hours. Evaporate the solution, extract the resultant residue with hot aqueous ethanol then evaporate the combined extracts and chromatograph the resultant residue over 10 gm. of silica gel eluting with the lower phase of a 2:1:1 mixture of chloroform-methanol-15% ammonium hydroxide. Combine and evaporate the like fractions as determined by thin layer chromatography to obtain 1-N-methylgentamicin $C_1$.

EXAMPLE 9

A. In a manner similar to that described in Example 1A treat each of the following 4,6-diaminoglycosyl-1,3-diaminocyclitols in water with sulfuric acid followed by acetaldehyde and sodium cyanoborohydride:
1. gentamicin A,
2. gentamicin B,
3. gentamicin $B_1$,
4. gentamicin $C_1$,
5. gentamicin $C_{1a}$,
6. gentamicin $C_2$,
7. gentamicin $C_{2a}$,
8. gentamicin $C_{2b}$,
9. gentamicin $X_2$,
10. Antibiotic G-418,
11. Antibiotic JI-20A,
12. Antibiotic JI-20B,
13. tobramycin,
14. Antibiotic 66-40B,
15. Antibiotic 66-40D,
16. mutamicin 1,
17. mutamicin 2,
18. mutamicin 4,
19. mutamicin 5,
20. mutamicin 6.

Isolate and purify each of the resultant products in a manner similar to that described in Example 1A to obtain the corresponding 1-N-ethyl compound, i.e.
1. 1-N-ethylgentamicin A,
2. 1-N-ethylgentamicin B,
3. 1-N-ethylgentamicin $B_1$,
4. 1-N-ethylgentamicin $C_1$,
5. 1-N-ethylgentamicin $C_{1a}$,
6. 1-N-ethylgentamicin $C_2$,
7. 1-N-ethylgentamicin $C_{2a}$,
8. 1-N-ethylgentamicin $C_{2b}$,
9. 1-N-ethylgentamicin $X_2$,
10. 1-N-ethyl Antibiotic G-418,
11. 1-N-ethyl Antibiotic JI-20A,
12. 1-N-ethyl Antibiotic JI-20B,
13. 1-N-ethyltobramycin,
14. 1-N-ethyl Antibiotic 66-40B,
15. 1-N-ethyl Antibiotic 66-40D,
16. 1-N-ethylmutamicin 1,
17. 1-N-ethylmutamicin 2,
18. 1-N-ethylmutamicin 4,
19. 1-N-ethylmutamicin 5,
20. 1-N-ethylmutamicin 6.

B. In the procedure of Example 9A by utilizing propanal in place of acetaldehyde there is obtained the corresponding 1-N-(n-propyl) derivative of each of the 4,6-diaminoglycosyl-1,3-diaminocyclitols listed therein.

C. By treating each of the aminoglycoside starting compounds listed in Example 9A with 4-acetamidobutanal or 3-acetamidopropanal according to the procedures of Examples 1-I and 1-L there is obtained the corresponding 1-N- (δ-aminobutyl)- and 1-N- (γ-aminopropyl)-derivative, respectively thereof.

D. By treating each of the 4,6-diaminoglycosyl- 1,3-diaminocyclitol starting compounds listed in above Example 9A in a manner similar to that described in any of Examples 1A through 1L there is obtained the corresponding 1-N-alkyl derivative thereof.

EXAMPLE 10

Acid Addition Salts

A. Sulfate Salts (Sulfuric acid addition salts)

Dissolve 5.0 grams of 1-N-ethylsisomicin in 25 ml. of water and adjust the pH of the solution to 4.5 with 1N sulfuric acid. Pour into about 300 milliters of methanol with vigorous agitation, continue the agitation for about 10–20 minutes and filter. Wash the precipitate with methanol and dry at about 60° C in vacuo to obtain 1-N-ethylsisomicin sulfate.

In like manner, the sulfate salt of the compounds of Examples 1–9 may also be prepared.

B. Hydrochloride Salts

Dissolve 5.0 grams of 1-N-ethylverdamicin in 25 milliters of water. Acidify with 2 N-hydrochloric acid to pH 5. Lyophilize to obtain 1-N-ethylverdamicin hydrochloride.

In like manner, the hydrochloride salt of the compounds of Examples 1–9 may also be prepared.

The present invention includes within its scope pharmaceutical compositions comprising our novel 1-N-X-4,6-di- (aminoglycosyl)-1,3-diaminocyclitols with a compatible, pharmaceutically acceptable carrier or coating. Also included within out invention is the method of eliciting an antibacterial response in a warm-blooded animal having a susceptible bacterial infection which comprises administering to said animal a nontoxic, antibacterially effective amount of a member selected from the group consisting of a 1-N-X-gentamicin A, 1-N-X-gentamicin B, 1-N-X-gentamicin $B_1$, 1-N-X-gentamicin $C_1$, 1-N-X-gentamicin $C_{1a}$, 1-N-X-gentamicin $C_2$, 1-N-X-gentamicin $C_{2a}$, 1-N-X-gentamicin $C_{2b}$, 1-N-X-gentamicin $X_2$, 1-N-X-sisomicin, 1-N-X-verdamicin, 1-N-X-tobramycin, 1-N-X-Antibiotic G-418, 1-N-X-Antibiotic 66-40B, 1-N-X-Antibiotic 66-40D, 1-N-X-Antibiotic JI-20A, 1-N-X-Antibiotic JI-2oB, 1-N-X-Antibiotic G-52, 1-N-X-mutamicin 1, 1-N-X-mutamicin 2, 1-N-X-mutamicin 4, 1-N-X-mutamicin 5, 1-N-X-mutamicin 6, wherein X is an alkyl substituent selected from the group consisting of alkyl, cycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms and, when said alkyl substituent is substituted by both hydroxyl and amino functions, only one of said functions can be attached to any one carbon atom, and pharmaceutically acceptable acid addition salts thereof. As discussed hereinabove, the 1-N-alkyl-4,6-di-(amino-glycosyl)-1,3-diaminocyclitols of this invention such a defined by formulae I, II, III, IV, and V and the non-toxic pharmaceutically acceptable acid addition salts thereof are broad spectrum antibacterial agents which, advantageously, exhibit activity against organisms, particularly gram-negative organisms, which are resistant to their 1-N-unsubstituted precursors. Thus, the compounds of this invention can be used alone or in combination with other antibiotic agents to prevent the growth or reduce the number of bacteria in various environments. They may be used, for example, to disinfect laboratory glassware, dental and medical equipment contaminated with *Staphylococcus aureus or other bacteria inhibited by the* 1-N-alkyl derivatives of this invention. The activity of the 1-N-alkyl-4,6-di-(aminoglycosyl)-1,3-diaminocyclitols against gram negative bacteria renders them useful for combating infections caused by gram negative organisms, e.g. species of Proteus and Pseudomonas. Our 1-N-alkyl-4,6-di-(aminoglycosyl)-1,3-diaminocyclitols, e.g. 1-N-ethylsisomicin and 1-N-ethylverdamicin have veterinary applications, particularly in the treatment of mastitis in cattle and Salmonella induced diarrhea in domestic animals such as the dog and the cat.

In general, the dosage administered of the 1-N-alkyl-4,6-di-(aminoglycosyl)-1,3-diaminocyclitols will be dependent upon the age and weight of the animal species being treated, the mode of administration, and the type and severity of bacterial infection being prevented or reduced. In general, the dosage of 1-N-alkyl-4,6-di-(aminoglycosyl)-1,3-diaminocyclitols employed to combat a given bacterial infection will be similar to the dosage requirements of the corresponding 1-N-unsubstituted-4,6-di-(aminoglycosyl)-1,3-diaminocyclitols. Additionally, the 1-N-alkyl-4,6-di-(aminoglycosyl)-1,3-diaminocyclitols of formulae I, II, III, IV and V, particularly those defined by formula I, e.g. 1-N-alkyl sisomicin and 1-N-alkylverdamicin wherein said alkyl has up to 4 carbon atoms especially the 1-N-ethyl-, 1-N-propyl and 1-N(δ-aminobutyl)- derivatives, are also advantageously cidal against certain gram negative organisms which are resistant to the 1-N-unsubstituted precursors.

The 1-N-alkyl-4,6-di-(aminoglycosyl)-1,3-diaminocyclitols of formulae I, II, III, IV and V and the pharmaceutically acceptable acid addition salts thereof may be administered orally. They may also be applied topically in the form of ointments, both hydrophilic and hydrophobic, in the form of lotions which may be aqueous, non-aqueous or of the emulsion type or in the form of creams. Pharmaceutical carriers useful in the preparation of such formulations will include, for example such substances as water, oils, greases, polyesters, polyols and the like.

For oral administration the 1-N-alkyl-4,6-di-(aminoglycosyl)-1,3-diammocyclitols antibacterials of this invention may be compounded in the form of tablets, capsules, elixirs or the like or may even be admixed with animal feed. It is in these dosage forms that the antibacterials are most effective for treating bacterial infections of the gastrointestinal tract which infections cause diarrhea.

In general, the topical preparations will contain from about 0.1 to about 3.0 gms. of 1-N-alkyl-4,6-di-(aminoglycosyl)-1,3-diaminocyclitols of formulae I, II, III, IV and V per 100 gms. of ointment, creams or lotion. The topical preparations are usually applied gently to lesions from about 2 to about 5 times a day.

The antibacterials of this invention may be utilized in liquid form such as solutions, suspensions and the like for otic and optic use and may also be administered parenterally via intramuscular injection. The injectable solution or suspension will usually be administered at from about 1 mg. to about 15 mgs. of antibacterial per kilograms of body weight per day divided into about 2 to about 4 doses. The precise dose depends on the stage and severity of the infection, the susceptibility of the infecting organism to the antibacterial and the individual characteristics of the animal species being treated.

The following formulations are to exemplify some of the dosage forms in which the antibacterial agents of this invention and their derivatives may be employed:

Formulation 1

| Tablet | 10 mg. Tab. | 25 mg. Tab. | 100 mg. Tab. |
|---|---|---|---|
| 1-N-ethylsisomicin | 10.50* mg. | 26.25* mg. | 105.00* mg. |
| Lactose, impalpable powder | 197.50 mg. | 171.25 mg. | 126.00 mg. |
| Corn Starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |

*5% excess

Procedure

Prepare a slurry consisting of the 1-N-ethylsisomicin, lactose and polyvinylpyrrolidone. Spray dry the slurry. Add the corn starch and magnesium stearate. Mix and compress into tablets.

Formulation 2

| Ointment | |
|---|---|
| 1-N-ethylverdamicin | 1.0 gm. |
| Methyl paraben U.S.P. | 0.5 gm. |
| Propyl paraben U.S.P. | 0.1 gm. |
| Petrolatum | to 1000 gm. |

Procedure

1. Melt the petrolatum.
2. Mix the 1-N-ethylverdamicin, methyl paraben and propyl paraben with about 10% of the molten petrolatum.
3. Pass the mixture through a colloid mill.
4. Add the remainder of the petrolatum with agitation and cool the mixture until it becomes semi-solid. At this stage the product may be put into suitable containers.

Ointments of 1-N-alkyl-4,6-di-(aminoglycosyl)-1,3-diaminocyclitols of formulae I, II, III, IV and V and of the acid addition salts thereof are prepared by substituting an equivalent quantity of 1-N-alkyl-4,6-di-(aminoglycosyl)-1,3-diaminocyclitols or acid addition salt for 1-N-ethylverdamicin in the foregoing example and by following substantially the procedure of the example.

Formulation 3

| Injectable Solution | Per 2.0 ml. vial | Per 50 Liters |
| --- | --- | --- |
| 1-N-ethylsisomicin sulfate | 84.0 mgs.* | 2100.0* gms. |
| Methyl paraben, U.S.P. | 3.6 mgs. | 90.0 gms. |
| Propyl paraben, U.S.P. | 0.4 mgs. | 10.0 gms. |
| Sodium bisulfite, U.S.P. | 6.4 mgs. | 160.0 gms. |
| Disodium Ethylenediamine tetraacetate dihydrate, R.G. | 0.2 mgs. | 5.0 gms. |
| Water, U.S.P. q.s. | 2.0 ml. | 50.0 liters |

*Includes a 5% manufacturing overcharge.

Procedure: For a 50.0 liter batch

Charge approximately 35 liters of water for injection to a suitable stainless steel jacketed vessel and heat to about 70° C. Charge the methylparaben and propylparaben to the heated water for injection and dissolve with agitation. When the parabens are completely dissolved, cool the contents of the tank to 25°–30° C by circulating cold water through the tank jacket. Sparge the solution with nitrogen gas for at least 10 minutes and keep covered with nitrogen during subsequent processing. Charge and dissolve the disodium EDTA and sodium bisulfite. Charge and dissolve the 1-N-ethylsisomicin sulfate. Bring the batch volume up to 50.0 liters with water for injection and agitate until homogenous.

Under sterile conditions, filter the solutions through a suitable bacteria retentive filter collecting the filtrate in a filling tank.

Fill the filtrate aseptically into sterile pyrogen-free multiple dose vials, stopper and seal.

In like manner, injectable solutions of 1-N-propylsisomicin, 1-N-(δ-aminobutyl)sisomicin, 1-N-ethylverdamicin, 1-N-propylverdamicin and 1-N-(δ-aminobutyl)verdamicin and especially acid addition salts of such antibacterial agents, may be prepared by substituting an equivalent quantity of such compounds for 1-N-ethylsisomicin sulfate and by following the procedure set forth above.

We claim:

1. A compound selected from the group consisting of a 1-N-X-4,6-di-O-(aminoglycosyl)-1,3-diaminocyclitol selected from the group consisting of 1-N-X-gentamicin A, 1-N-X-gentamicin B, 1-X-gentamicin $B_1$, 1-N-X-gentamicin $C_1$, 1-N-X-gentamicin $C_{1a}$, 1-N-X-gentamicin $C_2$, 1-N-X-gentamicin $C_{2a}$, 1-N-X-gentamicin $C_{2b}$, 1-N-X-gentamicin $X_2$, 1-N-X-sisomicin, 1-N-X-verdamicin, 1-N-X-tobramycin, 1-N-X-Antibiotic G-418, 1-N-X-Antibiotic 66-40B, 1-N-X-Antibiotic 66–40D, 1-N-X-Antibiotic JI-20A, 1-N-X-Antibiotic JI-20B, 1-N-X-Antibiotic G-52, 1-N-X-mutamicin 1, 1-N-X-mutamicin 2, 1-N-X-mutamicin 4, 1-N-X-mutamicin 5, and 1-N-X-mutamicin 6;

wherein X is an alkyl substituent selected from the group consisting of alkyl, cycloalkylalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom; and the pharmaceutically acceptable acid addition salts thereof.

2. A compound of claim 1 wherein X is an alkyl having up to 4 carbon atoms.

3. A compound of claim 1 wherein said 6-aminoglycosyl is garosaminyl.

4. A compound of claim 1 wherein said 6-O-aminoglycosyl is 6-O-garosaminyl and said 1,3-diaminocyclitol is 2-deoxystretpamine, said compound being a 1-N-X-4-O-aminoglycosyl-6-O-garosaminyl-2-deoxystreptamine selected from the group consisting of 1-N-X-gentamicin B, 1-N-X-gentamicin $B_1$, 1-N-X-gentamicin $C_1$, 1-N-X-gentamicin $C_{1a}$, 1-N-X-gentamicin $C_2$, 1-N-X-gentamicin $C_{2a}$, 1-N-X-gentamicin $C_{2b}$, 1-N-X-gentamicin $X_2$, 1-N-X-sisomicin, 1-N-X-verdamicin, 1-N-X-Antibiotic G-418, 1-N-X-Antibiotic JI-20A, 1-N-X-Antibiotic JI-20B, and 1-N-X-Antibiotic G-52, X being an alkyl substituent as defined in claim 1.

5. 1-N-(γ-aminopropyl)-4-O-aminoglycosyl-6O-garosaminyl-2-deoxystreptamine of claim 4.

6. 1-N-(δ-aminobutyl)-4-O-aminoglycosyl-6-O-garosaminyl-2-deoxystreptamine of claim 4.

7. 1-N-ethyl-4-O-aminoglycosyl-6-O-garosaminyl-2-deoxystreptamine of claim 4.

8. 1-N-propyl-4O-aminoglycosyl-6-O-garosaminyl-2-deoxystreptamine of claim 4.

9. 1-N-X-4O-aminoglycosyl-6-O-garosaminyl-2-deoxystreptamine of claim 4 wherein X is an aminohydroxyalkyl having up to 4 carbon atoms.

10. 1-N-(S-δ-hydroxy-δ-aminobutyl)-4-O-aminoglycosyl-6-O-garosaminyl-2-deoxystreptamine of claim 9.

11. 1-N-(S-β-hydroxy-γ-aminopropyl)-4-O-aminoglycosyl-6-O-garosaminyl-2-deoxystreptamine of claim 9.

12. A compound of claim 7 which is 1-N-ethylsisomicin.

13. A compound of claim 7 which is 1-N-ethylverdamicin.

14. A compound of claim 7 which is 1-N-ethylgentamicin $C_{1a}$.

15. A compound of claim 7 which is 1-N-ethylgentamicin $C_1$.

16. A compound of claim 7 which is 1-N-ethyl-Antibiotic G-52.

17. A compound of claim 8 which is 1-N-(n-propyl)-sisomicin.

18. A compound of claim 6 which is 1-N-(δ-aminobutyl)sisomicin.

19. A compound of claim 2 which is 1-N-methylsisomicin.

20. A compound of claim 2 which is 1-N-methylverdamicin.

21. A compound of claim 8 which is 1-N-(n-propyl)-verdamicin.

22. A compound of claim 6 which is 1-N-(δ-aminobutyl)-verdamicin.

23. A compound of claim 10 which is 1-N-S-β-hydroxy-δ-aminobutyl)-gentamicin $C_1$.

24. A compound of claim 10 which is 1-N-(S-β-hydroxy-δ-aminobutyl)-sisomicin.

25. A compound of claim 10 which is 1-N-(S-β-hydroxy-δ-aminobutyl)-verdamicin.

26. A compound of claim 4 which is 1-N-X-sisomicin.

27. A compound of claim 4 which is 1-N-X-verdamicin.

28. A compound of claim 1 which is 1-N-X-Antibiotic 66–40D.

29. A compound of claim 5 which is 1-N-(γ-aminopropyl)-sisomicin.

30. A compound of claim 5 which is 1-N-(γ-aminopropyl)-verdamicin.

31. The process for the preparation of a 1-N-X-4,6-di-O-(aminoglycosyl)-1,3-diaminocyclitol wherein X is an alkyl substituent selected from the group consisting of alkyl, cycloalkylalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom; which comprises the reaction of an acid addition salt of a 4,6-di-O-(aminoglycosyl)-1,3-diaminocyclitol antibacterial agent with one equivalent of a hydride-donor reducing agent selected from the group consisting of dialkylaminoborane, tetraalkylammonium cyanoborohydride, alkali metal cyanoborohydride, and alkali metal borohydride in an inert solvent and with at least one quivalent of an aldehyde having the formula X'CHO wherein X' is a member selected from the group consisting of hydrogen and an alkyl substituent selected from the group consisting of alkyl, cycloalkyl, alkenyl, aralkyl, hydroxyalkyl, aminoalkyl, alkylaminoalkyl, aminohydroxyalkly, and alkylaminohydroxyalkyl, said alkyl substituent having up to 7 carbon atoms, and, when said alkyl substituent is substituted by both hydroxyl and amino functions, only one of said functions can be attached to any one carbon atom;
followed by reaction with base of the thereby formed acid addition salt of the corresponding 1-N-X-4,6-di-O-(aminoglycosyl)-1,3-diaminocyclitol.

32. The process of claim 31 when said inert solvent is a protic solvent.

33. The process of claim 31 including the step of isolating the 1-N-X-4,6-di-O-(aminoglycosyl)-1,3-diaminocyclitol thereby formed.

34. The process of claim 31 wherein said hydride-donor reducing agent is an alkali metal cyanoborohydride, said inert solvent comprises water, and said 4,6-di-o-(aminoglycosyl)-1,3-diaminocyclitol is a compound selected from the group consisting of gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, tobramycin, Antibiotic G-418, Antibiotic 66-40B, Antibiotic 66-40D, Antibiotic JI-20A, Antibiotic JI-20B, Antibiotic G-52, mutamicin 1, mutamicin 2, mutamicin 4, mutamicin 5, and mutamicin 6.

35. The process of claim 34 wherein said aldehyde is a compound of formula X'CHO wherein X' is α-hydroxy-γ-aminopropyl.

36. The process of claim 34 wherein siad aldehyde is a compound of the formula X'CHO wherein X' is methyl or ethyl.

37. The process for preparing a 1-N-X-4,6-di-O-(aminoglycosyl)-1,3-diaminocyclitol wherein X is an alkyl substituent selected from the group consisting of alkyl, cycloakylalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted and, when said alkyl is substituted by both hydroxyl and amino functions, only one of said functions can be attached at any one carbon atom; which process comprises the reaction of an amide-reducing hydride reagent in a non-reactive organic solvent with the corresponding 1-N-acyl-4,6-di-O-(aminoglycosyl)-1,3-diaminocyclitol, said acyl having the formula X' —CO— wherein X' is a member selected from the group consisting of hydrogen, and an alkyl substituent selected from the group consisting of alkyl, cycloalkyl, alkenyl, aralkyl, hydroxyalkyl, aminoalkyl, alkylaminoalkyl, aminohydroxyalkyl, and alkylaminohydroxyalkyl, said alkyl substituent having up to 7 carbon atoms, and, when said alkyl substituent is substituted by both hydroxyl and amino functions, only one of said functions can be attached to any one carbon atom.

38. The process of claim 37 including the step of isolating the 1-N-X-4,6-di-O-(aminoglycosyl)-1,3-diaminocyclitol thereby formed.

39. The process of claim 37 wherein said amide-reducing hydride reagent is an amide-reducing aluminum hydride reagent or an amide-reducing borohydride reagent.

40. The process of claim 37 wherein said amide-reducing hydride reagent is lithium aluminum hydride.

41. The process of claim 37 wherein said amide-reducing borohydride reagent is diborane.

42. The process of claim 37 wherein said 1-N-acyl-4,6-di-O-(aminoglycosyl)-1,3-diaminocyclitol is a member selected from the group consisting of a 1-N-acylgentamicin A, 1-N-acylgentamicin B, 1-N-acylgentamicin $B_1$, 1-N-acylgentamicin $C_1$, 1-N-acylgentamicin $C_{1a}$, 1-N-acylgentamicin $C_{C2}$, 1-N-acylgentamicin $C_{2a}$, 1-N-acylgentamicin $C_{2b}$, 1-N-acylgentamicin $X_2$, 1-N-acylsisomicin, 1-N-acylverdamicin, 1-N-acyltobramycin, 1-N-acyl-Antibiotic G-418, 1-N-acyl-Anitibiotic 66-40B, 1-N-acyl-Antibiotic 66-40D, 1-N-acyl-Antibiotic JI-20A, 1-N-acyl-Antibiotic JI-20B, 1-N-acyl-Antibiotic G-52, 1-N-acylmutamicin 1, 1-N-acylmutamicin 2, 1-N-acymutamicin 4, 1-N-acylmutamicin 5, and 1-N-acylmutamicin 6.

43. The method of eliciting an antibacterial response in a warm-blooded animal having a susceptible bacterial infection, which comprises administering to said animal a non-toxic, antibacterially effective amount of a member selected from the group consisting of a 1-N-X-4,6-di-O-(aminoglycosyl)-1,3-diaminocyclitol selected from the group consiting of 1-N-X-gentamicin A, 1-N-X-gentamicin B, 1-N-X-gentamicin $B_1$, 1-N-X-gentamicin $C_1$, 1-N-X-gentamicin $C_{1a}$, 1-N-X-gentamicin $C_2$, 1-N-X-gentamicin $C_{2a}$, 1-N-X-gentamicin $C_{2b}$, 1-N-X-gentamicin $X_2$, 1-N-X-sisomicin, 1-N-X-verdamicin, 1-N-X-tobramycin, 1-N-X-Antibiotic G-418, 1-N-X-Antibiotic 66-40B, 1-N-X-Antibiotic 66-40D, 1-N-X-Antibiotic JI-20A, 1-N-X-Antibiotic JI-20B, 1-N-X-Antibiotic G-52, 1-N-X-mutamicin 1, 1-N-X-mutamicin 2, 1-N-X-mutamicin 4, 1-N-X-mutamicin 5, and 1-N-X-mutamicin 6;

wherein X is an alkyl substituent selected from the group consisting of alkyl, cycloalkylalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substitutent adjacent to the aminoglycoside nitrogen being unsubstituted, and when said alkyl substituent is substituted by both hydroxyl and amino functions, only one of said functions can be attached at any one carbon atom; and the pharmaceutically acceptable acid addition salts thereof.

44. The method of claim 43 when carried out with a 1-N-X-4,6-di-O-(aminoglycosyl)-1,3-diaminocyclitol wherein X is a lower alkyl having up to 4 carbon atoms.

45. The method of claim 43 when carried out with 1N-ethylverdamicin.

46. The method of claim 43 when carried out with 1-N-ethylsisomicin.

47. A pharmaceutical composition comprising an antibacterially effective amount of a member selected from the group consisting of 1-N-X-gentamicin A, 1-N-X-gentamicin B, 1-N-X-gentamicin $B_1$, 1-N-X-gentamicin $C_1$, 1-N-X-gentamicin $C_{1a}$, 1-N-X-gentamicin $C_2$, 1-N-X-gentamicin $C_{2a}$, 1-N-X-gentamicin $C_{2b}$, 1N-X-gentamicin $X_2$, 1N-X-sisomicin, 1-N-X-verdamicin, 1-N-X-tobramycin, 1-N-X-Antibiotic G-418, 1-N-X-Antibiotic 66-40B, 1-N-X-Antibiotic 66-40D, 1-N-X-Antibiotic JI-20A, 1-N-X-Antibiotic JI-20B, 1-N-X-Antibiotic G-52, 1-N-X-mutamicin 1, 1-N-X-mutamicin 2, 1-N-X-mutamicin 4, 1-N-X-mutamicin 5, and 1-N-X-mutamicin 6;

wherein X is an alkyl substituent selected from the group consisting of alkyl, cycloalkylalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom; and the pharmaceutically acceptable acid addition salts thereof;

together with a non-toxic pharmaceutically acceptable carrier.

* * * * *

UNITED STATES PATENT OFFICE
CERTIFICATE OF CORRECTION

Patent No. 4,002,742                    Dated January 11, 1977

Inventor(s) John J. Wright et al

It is certified that error appears in the above-identified patent and that said Letters Patent are hereby corrected as shown below:

Title, line 2 of title, "-1,3-DIAMINOCYCLITOS,-" should read ---1,3-DIAMINOCYCLITOLS,---. Column 1, line 2 of title, "DIAMINOCYCLITOS," should read ---DIAMINOCYCLITOLS,---. Column 16, line 12, "-$C_2H_{41}N_5O_7$;-" should read ---$C_{20}H_{41}N_5O_7$;---. Column 17, line 24, "332, 304," should read ---332, 322, 304,---. Column 20, line 16, "cm$^-$" should read ---cm$^{-1}$---; line 36, "cm$^-$" should read ---cm$^{-1}$---. Column 24, line 10, "1. 1-$\underline{N}$-(=-" should read ---1. 1-$\underline{N}$-(β---; line 42, "6. 1-$\underline{N}$-($\omega$-hydroxycotyl)-" should read ---6. 1-$\underline{N}$-($\omega$-hydroxyoctyl)---. Column 27, line 35, "3.5Hz,1')" should read ---3.5Hz, $H_1$')---; line 66, "65 g." should read -65 mg.---; line 67, "in vacuo of about" should read ---in vacuo to a volume of about---. Column 28, line 27, "J=4.00Hz," should read ---J=4.0Hz,---; line 28, "-M+1)$^+$" should read ---(M+1)$^+$---. Column 29, last line and Column 30, line 1, "hydroxyacetaldehyde, and phenylacetaldehyde," should read ---hydroxyacetaldehyde, 4-hydroxybutanal, and phenylacetaldehyde ---. Column 40, line 45, Claim 10, "-(S-$\delta$-hydroxy-$\delta$-" should read ---(S-β-hydroxy-$\delta$---. Column 42, line 48, Claim 42, "gentamicin $Cc_2$," should read ---gentamicin $C_{2r}$---.

Signed and Sealed this

Nineteenth Day of April 1977

[SEAL]

Attest:

RUTH C. MASON
*Attesting Officer*

C. MARSHALL DANN
*Commissioner of Patents and Trademarks*